US011111508B2

(12) United States Patent
Lau

(10) Patent No.: US 11,111,508 B2
(45) Date of Patent: Sep. 7, 2021

(54) MODIFIED CAS9 COMPOSITIONS AND METHODS OF USE

(71) Applicant: BRANDEIS UNIVERSITY, Waltham, MA (US)

(72) Inventor: Nelson Lau, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 730 days.

(21) Appl. No.: 15/762,025

(22) PCT Filed: Oct. 25, 2016

(86) PCT No.: PCT/US2016/058719
§ 371 (c)(1),
(2) Date: Mar. 21, 2018

(87) PCT Pub. No.: WO2017/074962
PCT Pub. Date: May 4, 2017

(65) Prior Publication Data
US 2018/0265895 A1 Sep. 20, 2018

Related U.S. Application Data

(60) Provisional application No. 62/249,113, filed on Oct. 30, 2015.

(51) Int. Cl.
*C12N 15/90* (2006.01)
*C12N 9/22* (2006.01)
*C12N 15/11* (2006.01)

(52) U.S. Cl.
CPC ............. *C12N 15/907* (2013.01); *C12N 9/22* (2013.01); *C12N 15/11* (2013.01); *C07K 2319/00* (2013.01); *C12N 2310/20* (2017.05)

(58) Field of Classification Search
CPC ........ C12N 15/907; C12N 15/11; C12N 9/22; C12N 2310/20; C07K 2319/00

USPC .................. 435/196, 455; 530/350
See application file for complete search history.

(56) References Cited

U.S. PATENT DOCUMENTS

| | | | |
|---|---|---|---|
| 2014/0342456 A1 | 11/2014 | Mali et al. | |
| 2014/0356867 A1 | 12/2014 | Peter et al. | |
| 2015/0071898 A1 | 3/2015 | Liu et al. | |
| 2017/0306307 A1* | 10/2017 | Zhang | C12N 15/102 |
| 2018/0187172 A1* | 7/2018 | Bleris | C12N 15/111 |
| 2019/0249230 A1* | 8/2019 | Pederson | C12N 15/85 |

FOREIGN PATENT DOCUMENTS

WO     2016061523 A1     4/2016

OTHER PUBLICATIONS

Nissim, L. et al., "Multiplexed and Programmable Regulation of Gene Networks with an Integrated RNA and CRISPR/Cas Toolkit in Human Cells," Molecular Cell, May 15, 2014, vol. 54, No. 4, pp. 698-710, p. 4, paragraph 4, Genbank supplement pp. 1-4: DOI: 10.1016/j.molcel.2014.0422.
Ruan, J. et al., Highly Efficient CRISPR/Cas9-Mediated Transgene Knockin at the H11 Locus in Pigs, Scientific Reports, Sep. 18, 2015; vol. 5, No. 14253; pp. 1-10; abstract; p. 2, paragraph 3, p. 3, paragraph 1; p. 6, paragraph 4; p. 8, paragraph 6-p. 9, paragraph 1: DOI: 10.1038/srep14253.
International Search Report and Written Opinion for corresponding PCT/US16/58719, dated Feb. 7, 2017 (16 pages).

\* cited by examiner

*Primary Examiner* — Anne Marie S Wehbe
(74) *Attorney, Agent, or Firm* — Cantor Colburn LLP

(57) ABSTRACT

The invention features Cas9 fusion polypeptides. In one embodiment of the invention, Cas9 is fused to a SNAP tag that enhances Cas9's gene repair function.

7 Claims, 9 Drawing Sheets

Specification includes a Sequence Listing.

SEQUENCE LISTING

<160> NUMBER OF SEQ ID NOS: 4

<210> SEQ ID NO 1
<211> LENGTH: 4722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atggacaaga agtactccat tgggctcgat atcggcacaa acagcgtcgg ctgggccgtc    60
attacggacg agtacaaggt gccgagcaaa aaattcaaag ttctgggcaa taccgatcgc   120
cacagcataa agaagaacct cattggcgcc ctcctgttcg actccgggga gacggccgaa   180
gccacgcggc tcaaaagaac agcacggcgc agatataccc gcagaaagaa tcggatctgc   240
tacctgcagg agatctttag taatgagatg gctaaggtgg atgactcttt cttccatagg   300
ctggaggagt ccttttttggt ggaggaggat aaaaagcacg agcgccaccc aatctttggc   360
aatatcgtgg acgaggtggc gtaccatgaa aagtacccaa ccatatatca tctgaggaag   420
aagcttgtag acagtactga taaggctgac ttgcggttga tctatctcgc gctggcgcat   480
atgatcaaat ttcggggaca cttcctcatc gagggggacc tgaacccaga caacagcgat   540
gtcgacaaac tctttatcca actggttcag acttacaatc agcttttcga agagaacccg   600
atcaacgcat ccggagttga cgccaaagca atcctgagcg ctaggctgtc caaatcccgg   660
cggctcgaaa acctcatcgc acagctccct ggggagaaga gaacggcct gtttggtaat   720 cttatcgccc tgtcactcgg gctgaccccc aactttaaat ctaacttcga cctggccgaa   780
gatgccaagc ttcaactgag caaagacacc tacgatgatg atctcgacaa tctgctggcc   840 cagatcgcg accagtacgc agacctttt ttggcggcaa agaacctgtc agacgccatt   900
ctgctgagtg atattctgcg agtgaacacg gagatcacca agctccgct gagcgctagt   960 atgatcaagc gctatgatga gcaccaccaa gacttgactt tgctgaaggc ccttgtcaga  1020
cagcaactgc ctgagaagta caaggaaatt ttcttcgatc agtctaaaaa tggctacgcc  1080
ggatacattg acggcggagc aagccaggag gaattttaca aatttattaa gcccatcttg  1140
gaaaaaatgg acggcaccga ggagctgctg gtaaagctta acagagaaga tctgttgcgc  1200
aaacagcgca ctttcgacaa tggaagcatc ccccaccaga ttcacctggg cgaactgcac  1260
gctatcctca ggcggcaaga ggatttctac ccctttttga aagataacag ggaaaagatt  1320
gagaaaatcc tcacatttcg gatacctac tatgtaggcc ccctcgcccg gggaaattcc  1380
agattcgcgt ggatgactcg caaatcagaa gagaccatca ctccctggaa cttcgaggaa  1440
gtcgtggata agggggcctc tgcccagtcc ttcatcgaaa ggatgactaa ctttgataaa  1500
aatctgccta acgaaaaggt gcttcctaaa cactctctgc tgtacgagta cttcacagtt  1560
```

-continued

```
tataacgagc tcaccaaggt caaatacgtc acagaaggga tgagaaagcc agcattcctg    1620
tctggagagc agaagaaagc tatcgtggac ctcctcttca agacgaaccg gaaagttacc    1680
gtgaaacagc tcaaagaaga ctatttcaaa aagattgaat gtttcgactc tgttgaaatc    1740
agcggagtgg aggatcgctt caacgcatcc ctgggaacgt atcacgatct cctgaaaatc    1800
attaaagaca aggacttcct ggacaatgag gagaacgagg acattcttga ggacattgtc    1860
ctcacccttt cgttgtttga agatagggag atgattgaag aacgcttgaa aacttacgct    1920
catctcttcg acgacaaagt catgaaacag ctcaagaggc gccgatatac aggatggggg    1980
cggctgtcaa gaaaactgat caatgggatc cgagacaagc agagtggaaa gacaatcctg    2040
gattttctta agtccgatgg atttgccaac cggaacttca tgcagttgat ccatgatgac    2100
tctctcacct ttaaggagga catccagaaa gcacaagttt ctggccaggg ggacagtctt    2160
cacgagcaca tcgctaatct tgcaggtagc ccagctatca aaaagggaat actgcagacc    2220
gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggatcat    2520
atcgtgcccc agtctttttct caaagatgat tctattgata taaagtgtt gacaagatcc    2580 gataaaaata gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtgccccaaa ttctcgattc acgcatgaac    2820
accaagtacg atgaaaatga caaactgatt cgagaggtga agttattac tctgaagtct    2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaatagc aaggccaccg ctaagtactt cttttacagc    3120
aatattatga atttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga cccccaagaa tacgcgggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatcaagct tcgaaaaaaa cccatcgac    3540 tttctcgagg cgaaaggata taagaggtc aaaaaagacc tcatcattaa gcttcccaag    3600
tactctctct ttgagcttga aaacggccgg aaacgaatgc tcgctagtgc gggcgagctg    3660
cagaaaggta cgagctggc actgccctct aaatacgtta atttcttgta tctgccagc    3720 cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
```

-continued

```
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agacagcagg gctgacccca agaagaagag gaaggtggct    4140
agcatggaca aagactgcga aatgaagcgc accaccctgg atagccctct gggcaagctg    4200
gaactgtctg ggtgcgaaca gggcctgcac cgtatcatct tcctgggcaa aggaacatct    4260
gccgccgacg ccgtggaagt gcctgcccca gccgccgtgc tgggcggacc agagccactg    4320
atgcaggcca ccgcctggct caacgcctac tttcaccagc ctgaggccat cgaggagttc    4380
cctgtgccag ccctgcacca cccagtgttc cagcaggaga gctttacccg ccaggtgctg    4440
tggaaactgc tgaaagtggt gaagttcgga gaggtcatca gctacagcca cctggccgcc    4500
ctggccggca atcccgccgc caccgccgcc gtgaaaaccg ccctgagcgg aaatcccgtg    4560
cccattctga tcccctgcca ccgggtggtg cagggcgacc tggacgtggg gggctacgag    4620
ggcgggctcg ccgtgaaaga gtggctgctg gcccacgagg ccacagact gggcaagcct    4680 gggctgggtg cggccgcact cgagcaccac caccaccacc ac                       4722
```

<210> SEQ ID NO 2
<211> LENGTH: 1574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640
```

-continued

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu

```
                1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

Ser Arg Ala Asp Pro Lys Lys Lys Arg Lys Val Ala Ser Met Asp
        1370                1375                1380

Lys Asp Cys Glu Met Lys Arg Thr Thr Leu Asp Ser Pro Leu Gly
        1385                1390                1395

Lys Leu Glu Leu Ser Gly Cys Glu Gln Gly Leu His Arg Ile Ile
        1400                1405                1410

Phe Leu Gly Lys Gly Thr Ser Ala Ala Asp Ala Val Glu Val Pro
        1415                1420                1425

Ala Pro Ala Ala Val Leu Gly Gly Pro Glu Pro Leu Met Gln Ala
        1430                1435                1440

Thr Ala Trp Leu Asn Ala Tyr Phe His Gln Pro Glu Ala Ile Glu
        1445                1450                1455
```

```
Glu Phe Pro Val Pro Ala Leu His His Pro Val Phe Gln Gln Glu
    1460                1465                1470

Ser Phe Thr Arg Gln Val Leu Trp Lys Leu Leu Lys Val Val Lys
    1475                1480                1485

Phe Gly Glu Val Ile Ser Tyr Ser His Leu Ala Ala Leu Ala Gly
    1490                1495                1500

Asn Pro Ala Ala Thr Ala Ala Val Lys Thr Ala Leu Ser Gly Asn
    1505                1510                1515

Pro Val Pro Ile Leu Ile Pro Cys His Arg Val Val Gln Gly Asp
    1520                1525                1530

Leu Asp Val Gly Gly Tyr Glu Gly Gly Leu Ala Val Lys Glu Trp
    1535                1540                1545

Leu Leu Ala His Glu Gly His Arg Leu Gly Lys Pro Gly Leu Gly
    1550                1555                1560

Ala Ala Ala Leu Glu His His His His His His
    1565                1570

<210> SEQ ID NO 3
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
```

-continued

```
                225                 230                 235                 240
        Leu Ile Ala Leu Ser Leu Gly Leu Thr Pro Asn Phe Lys Ser Asn Phe
                        245                 250                 255

Asp Leu Ala Glu Asp Ala Lys Leu Gln Leu Ser Lys Asp Thr Tyr Asp
                        260                 265                 270

Asp Asp Leu Asp Asn Leu Leu Ala Gln Ile Gly Asp Gln Tyr Ala Asp
                        275                 280                 285

Leu Phe Leu Ala Ala Lys Asn Leu Ser Asp Ala Ile Leu Leu Ser Asp
                        290                 295                 300

Ile Leu Arg Val Asn Thr Glu Ile Thr Lys Ala Pro Leu Ser Ala Ser
        305                 310                 315                 320

Met Ile Lys Arg Tyr Asp Glu His His Gln Asp Leu Thr Leu Leu Lys
                        325                 330                 335

Ala Leu Val Arg Gln Gln Leu Pro Glu Lys Tyr Lys Glu Ile Phe Phe
                        340                 345                 350

Asp Gln Ser Lys Asn Gly Tyr Ala Gly Tyr Ile Asp Gly Gly Ala Ser
                        355                 360                 365

Gln Glu Glu Phe Tyr Lys Phe Ile Lys Pro Ile Leu Glu Lys Met Asp
                        370                 375                 380

Gly Thr Glu Glu Leu Leu Val Lys Leu Asn Arg Glu Asp Leu Leu Arg
        385                 390                 395                 400

Lys Gln Arg Thr Phe Asp Asn Gly Ser Ile Pro His Gln Ile His Leu
                        405                 410                 415

Gly Glu Leu His Ala Ile Leu Arg Arg Gln Glu Asp Phe Tyr Pro Phe
                        420                 425                 430

Leu Lys Asp Asn Arg Glu Lys Ile Glu Lys Ile Leu Thr Phe Arg Ile
                        435                 440                 445

Pro Tyr Tyr Val Gly Pro Leu Ala Arg Gly Asn Ser Arg Phe Ala Trp
                        450                 455                 460

Met Thr Arg Lys Ser Glu Glu Thr Ile Thr Pro Trp Asn Phe Glu Glu
        465                 470                 475                 480

Val Val Asp Lys Gly Ala Ser Ala Gln Ser Phe Ile Glu Arg Met Thr
                        485                 490                 495

Asn Phe Asp Lys Asn Leu Pro Asn Glu Lys Val Leu Pro Lys His Ser
                        500                 505                 510

Leu Leu Tyr Glu Tyr Phe Thr Val Tyr Asn Glu Leu Thr Lys Val Lys
                        515                 520                 525

Tyr Val Thr Glu Gly Met Arg Lys Pro Ala Phe Leu Ser Gly Glu Gln
                        530                 535                 540

Lys Lys Ala Ile Val Asp Leu Leu Phe Lys Thr Asn Arg Lys Val Thr
        545                 550                 555                 560

Val Lys Gln Leu Lys Glu Asp Tyr Phe Lys Lys Ile Glu Cys Phe Asp
                        565                 570                 575

Ser Val Glu Ile Ser Gly Val Glu Asp Arg Phe Asn Ala Ser Leu Gly
                        580                 585                 590

Thr Tyr His Asp Leu Leu Lys Ile Ile Lys Asp Lys Asp Phe Leu Asp
                        595                 600                 605

Asn Glu Glu Asn Glu Asp Ile Leu Glu Asp Ile Val Leu Thr Leu Thr
                        610                 615                 620

Leu Phe Glu Asp Arg Glu Met Ile Glu Glu Arg Leu Lys Thr Tyr Ala
        625                 630                 635                 640

His Leu Phe Asp Asp Lys Val Met Lys Gln Leu Lys Arg Arg Arg Tyr
                        645                 650                 655
```

-continued

```
Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
675                 680                 685

Ala Asn Arg Asn Phe Met Gln Leu Ile His Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065
```

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
    1355                1360                1365

<210> SEQ ID NO 4
<211> LENGTH: 9524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gacgaaaggg cctcgtgata cgcctatttt tataggttaa tgtcatgata ataatggttt      60
cttagacgga tcgcttgcct gtaacttaca cgcgcctcgt atcttttaat gatggaataa     120
tttgggaatt tactctgtgt ttatttattt ttatgttttg tatttggatt ttagaaagta     180
aataaagaag gtagaagagt tacggaatga agaaaaaaaa ataaacaaag gtttaaaaaa     240

```
tttcaacaaa aagcgtactt tacatatata tttattagac aagaaaagca gattaaatag    300
atatacattc gattaacgat aagtaaaatg taaaatcaca ggattttcgt gtgtggtctt    360
ctacacagac aagatgaaac aattcggcat taatacctga gagcaggaag agcaagataa    420
aaggtagtat ttgttggcga tcccctaga gtcttttaca tcttcggaaa acaaaaacta    480
ttttttcttt aatttctttt tttacttttct attttttaatt tatatattta tattaaaaaa    540
tttaaattat aattattttt atagcacgtg atgaaaagga cccaggtggc acttttcggg    600
gaaatgtgcg cggaacccct atttgtttat ttttctaaat acattcaaat atgtatccgc    660
tcatgagaca ataaccctga taaatgcttc aataatattg aaaaggaag agtatgagta    720 ttcaacattt ccgtgtcgcc cttattccct tttttgcggc attttgcctt cctgtttttg    780
ctcacccaga aacgctggtg aaagtaaaag atgctgaaga tcagttgggt gcacgagtgg    840
gttacatcga actggatctc aacagcggta agatccttga gagttttcgc cccgaagaac    900
gttttccaat gatgagcact tttaaagttc tgctatgtgg cgcggtatta tcccgtattg    960
acgccgggca agagcaactc ggtcgccgca tacactattc tcagaatgac ttggttgagt   1020
actcaccagt cacagaaaag catcttacgg atggcatgac agtaagagaa ttatgcagtg   1080
ctgccataac catgagtgat aacactgcgg ccaacttact tctgacaacg atcggaggac   1140
cgaaggagct aaccgctttt ttgcacaaca tgggggatca tgtaactcgc cttgatcgtt   1200
gggaaccgga gctgaatgaa gccataccaa acgacgagcg tgacaccacg atgcctgtag   1260
caatggcaac aacgttgcgc aaactattaa ctggcgaact acttactcta gcttcccggc   1320
aacaattaat agactggatg gaggcggata agttgcagg accacttctg cgctcggccc   1380
ttccggctgg ctggtttatt gctgataaat ctggagccgg tgagcgtggg tctcgcggta   1440
tcattgcagc actggggcca gatggtaagc cctcccgtat cgtagttatc tacacgacgg   1500
ggagtcaggc aactatggat gaacgaaata gacagatcgc tgagataggt gcctcactga   1560
ttaagcattg gtaactgtca gaccaagttt actcatatat actttagatt gatttaaaac   1620 ttcatttta atttaaaagg atctaggtga agatccttt tgataatctc atgaccaaaa   1680
tcccttaacg tgagttttcg ttccactgag cgtcagaccc cgtagaaaag atcaaaggat   1740
cttcttgaga tcctttttt ctgcgcgtaa tctgctgctt gcaaacaaaa aaaccaccgc   1800
taccagcggt ggtttgtttg ccggatcaag agctaccaac tctttttccg aaggtaactg   1860
gcttcagcag agcgcagata ccaaatactg tccttctagt gtagccgtag ttaggccacc   1920
acttcaagaa ctctgtagca ccgcctacat acctcgctct gctaatcctg ttaccagtgg   1980
ctgctgccag tggcgataag tcgtgtctta ccgggttgga ctcaagacga tagttaccgg   2040
ataaggcgca gcggtcgggc tgaacggggg gttcgtgcac acagcccagc ttggagcgaa   2100
cgacctacac cgaactgaga tacctacagc gtgagctatg agaaagcgcc acgcttcccg   2160
aagggagaaa ggcggacagg tatccggtaa gcggcagggt cggaacagga gagcgcacga   2220
gggagcttcc agggggaaac gcctggtatc tttatagtcc tgtcgggttt cgccacctct   2280
gacttgagcg tcgatttttg tgatgctcgt cagggggggcg gagcctatgg aaaaacgcca   2340
gcaacgcggc cttttacgg ttcctggcct tttgctggcc ttttgctcac atgttctttc   2400
ctgcgttatc ccctgattct gtggataacc gtattaccgc ctttgagtga gctgataccg   2460
ctcgccgcag ccgaacgacc gagcgcagcg agtcagtgag cgaggaagcg gaagagcgcc   2520
caatacgcaa accgcctctc cccgcgcgtt ggccgattca ttaatgcagc tggcacgaca   2580
ggtttcccga ctggaaagcg ggcagtgagc gcaacgcaat taatgtgagt tacctcactc   2640
```

```
attaggcacc ccaggcttta cactttatgc ttccggctcc tatgttgtgt ggaattgtga    2700
gcggataaca atttcacaca ggaaacagct atgaccatga ttacgccaag cgcgcaatta    2760
accctcacta aagggaacaa aagctggagc tcatagcttc aaaatgtttc tactccttt t    2820 ttactcttcc agattttctc ggactccgcg catcgccgta ccacttcaaa acacccaagc    2880
acagcatact aaatttcccc tctttcttcc tctagggtgt cgttaattac ccgtactaaa    2940
ggtttggaaa agaaaaaaga gaccgcctcg tttcttttc ttcgtcgaaa aaggcaataa     3000 aaattttat cacgtttctt tttcttgaaa attttttttt tgatttttt ctctttcgat     3060 gacctcccat tgatatttaa gttaataaac ggtcttcaat ttctcaagtt tcagtttcat    3120
ttttcttgtt ctattacaac ttttttact tcttgctcat tagaaagaaa gcatagcaat     3180
ctaatctaag ttttctagaa ctagtggatc ccccgggaaa aatggacaag aagtactcca    3240
ttgggctcga tatcggcaca aacagcgtcg gttgggccgt cattacggac gagtacaagg    3300
tgccgagcaa aaaattcaaa gttctgggca ataccgatcg ccacagcata aagaagaacc    3360
tcattggcgc cctcctgttc gactccgggg agacggccga agccacgcgg ctcaaaagaa    3420
cagcacggcg cagatatacc cgcagaaaga atcggatctg ctacctgcag agatctttta   3480
gtaatgagat ggctaaggtg gatgactctt tcttccatag gctggaggag tccttttttgg   3540 tggaggagga taaaaagcac gagcgccacc caatctttgg caatatcgtg gacgaggtgg    3600
cgtaccatga aaagtaccca accatatatc atctgaggaa gaagcttgta gacagtactg    3660
ataaggctga cttgcggttg atctatctcg cgctggcgca tatgatcaaa tttcggggac    3720
acttcctcat cgagggggac ctgaacccag acaacagcga tgtcgacaaa ctctttatcc    3780
aactggttca gacttacaat cagcttttcg aagagaaccc gatcaacgca tccggagttg    3840
acgccaaagc aatcctgagc gctaggctgt ccaaatcccg gcggctcgaa aacctcatcg    3900
cacagctccc tggggagaag aagaacggcc tgtttggtaa tcttatcgcc ctgtcactcg    3960
ggctgacccc caactttaaa tctaacttcg acctggccga agatgccaag cttcaactga    4020
gcaaagacac ctacgatgat gatctcgaca atctgctggc ccagatcggc gaccagtacg    4080
cagacctttt tttggcggca aagaacctgt cagacgccat tctgctgagt gatattctgc    4140
gagtgaacac ggagatcacc aaagctccgc tgagcgctag tatgatcaag cgctatgatg    4200
agcaccacca agacttgact ttgctgaagg cccttgtcag acagcaactg cctgagaagt    4260
acaaggaaat ttcttcgat cagtctaaaa atggctacgc cggatacatt gacggcggag     4320
caagccagga ggaattttac aaattttatta agcccatctt ggaaaaaatg gacggcaccg    4380
aggagctgct ggtaaagctt aacagagaag atctgttgcg caaacagcgc actttcgaca    4440
atggaagcat ccccaccag attcacctgg gcgaactgca cgctatcctc aggcggcaag    4500
aggatttcta cccctttttg aaagataaca gggaaaagat tgagaaaatc ctcacatttc    4560 ggataccta ctatgtaggc cccctcgccc ggggaaattc cagattcgcg tggatgactc     4620
gcaaatcaga agagaccatc actccctgga acttcgagga agtcgtggat aagggggcct    4680
ctgcccagtc cttcatcgaa aggatgacta actttgataa aaatctgcct aacgaaaagg    4740
tgcttcctaa acactctctg ctgtacgagt acttcacagt ttataacgag ctcaccaagg    4800
tcaaatacgt cacagaaggg atgagaaagc cagcattcct gtctggagag cagaagaaag    4860
ctatcgtgga cctcctcttc aagacgaacc ggaaagttac cgtgaaacag ctcaaagaag    4920
actatttcaa aaagattgaa tgtttcgact ctgttgaaat cagcggagtg gaggatcgct    4980
```

```
tcaacgcatc cctgggaacg tatcacgatc tcctgaaaat cattaaagac aaggacttcc     5040
tggacaatga ggagaacgag gacattcttg aggacattgt cctcacccct acgttgtttg     5100 aagatagga gatgattgaa gaacgcttga aaacttacgc tcatctcttc gacgacaaag     5160
tcatgaaaca gctcaagagg cgccgatata caggatgggg gcggctgtca agaaaactga     5220
tcaatgggat ccgagacaag cagagtggaa agacaatcct ggattttctt aagtccgatg     5280
gatttgccaa ccggaacttc atgcagttga tccatgatga ctctctcacc tttaaggagg     5340
acatccagaa agcacaagtt tctggccagg gggacagtct tcacgagcac atcgctaatc     5400
ttgcaggtag cccagctatc aaaaagggaa tactgcagac cgttaaggtc gtggatgaac     5460
tcgtcaaagt aatgggaagg cataagcccg agaatatcgt tatcgagatg gcccgagaga     5520
accaaactac ccagaaggga cagaagaaca gtagggaaag gatgaagagg attgaagagg     5580
gtataaaaga actggggtcc caaatcctta aggaacaccc agttgaaaac cccagcttc     5640 agaatgagaa gctctacctg tactacctgc agaacggcag ggacatgtac gtggatcagg     5700
aactggacat caatcggctc tccgactacg acgtggatca tatcgtgccc cagtcttttc     5760
tcaaagatga ttctattgat aataaagtgt tgacaagatc cgataaaaat agagggaaga     5820
gtgataacgt ccctcagaa gaagttgtca gaaaatgaa aaattattgg cggcagctgc     5880
tgaacgccaa actgatcaca caacggaagt tcgataatct gactaaggct gaacgaggtg     5940
gcctgtctga gttggataaa gccggcttca tcaaaggca gcttgttgag acacgccaga     6000
tcaccaagca cgtggcccaa attctcgatt cacgcatgaa caccaagtac gatgaaaatg     6060
acaaactgat tcgagaggtg aaagttatta ctctgaagtc taagctggtc tcagatttca     6120
gaaaggactt tcagttttat aaggtgagag agatcaacaa ttaccaccat gcgcatgatg     6180
cctacctgaa tgcagtggta ggcactgcac ttatcaaaaa atatcccaag cttgaatctg     6240
aatttgttta cggagactat aaagtgtacg atgttaggaa aatgatcgca aagtctgagc     6300
aggaaatagg caaggccacc gctaagtact tcttttacag caatattatg aatttttcca     6360
agaccgagat tacactggcc aatggagaga ttcggaagcg accacttatc gaaacaaacg     6420
gagaaacaga gaaatcgtg tgggacaagg gtaggatt cgcgacagtc cggaaggtcc     6480
tgtccatgcc gcaggtgaac atcgttaaaa agaccgaagt acagaccgga ggcttctcca     6540
aggaaagtat cctcccgaaa aggaacagcg acaagctgat cgcacgcaaa aaagattggg     6600 acccaagaa atacggcgga ttcgattctc ctacagtcgc ttacagtgta ctggttgtgg     6660
ccaaagtgga gaaagggaag tctaaaaaac tcaaaagcgt caaggaactg ctgggcatca     6720
caatcatgga gcgatcaagc ttcgaaaaaa accccatcga cttctcgag gcgaaaggat     6780 ataaagaggt caaaaaagac ctcatcatta agcttcccaa gtactctctc tttgagcttg     6840
aaaacggccg gaaacgaatg ctcgctagtg cgggcgagct gcagaaaggt aacgagctgg     6900
cactgccctc taaatacgtt aatttcttgt atctggccag ccactatgaa aagctcaaag     6960
ggtctcccga agataatgag cagaagcagc tgttcgtgga acaacacaaa cactaccttg     7020
atgagatcat cgagcaaata agcgaattct ccaaaagagt gatcctcgcc gacgctaacc     7080
tcgataaggt gctttctgct tacaataagc acagggataa gcccatcagg gagcaggcag     7140
aaaacattat ccacttgttt actctgacca acttgggcgc gcctgcagcc ttcaagtact     7200
tcgacaccac catagacaga aagcggtaca cctctacaaa ggaggtcctg gacgccacac     7260
tgattcatca gtcaattacg gggctctatg aaacaagaat cgacctctct cagctcggtg     7320
gagacagcag ggctgacccc aagaagaaga ggaaggtgtg atctcttctc gagtcatgta     7380
```

```
attagttatg tcacgcttac attcacgccc tccccccaca tccgctctaa ccgaaaagga    7440
aggagttaga caacctgaag tctaggtccc tatttatttt tttatagtta tgttagtatt    7500
aagaacgtta tttatatttc aaattttcct ttttttctg tacagacgcg tgtacgcatg     7560
taacattata ctgaaaacct tgcttgagaa ggttttggga cgctcgaagg ctttaatttg    7620
cggccggtac ccaattcgcc ctatagtgag tcgtattacg cgcgctcact ggccgtcgtt    7680
ttacaacgtc gtgactggga aaaccctggc gttacccaac ttaatcgcct tgcagcacat    7740
ccccctttcg ccagctggcg taatagcgaa gaggcccgca ccgatcgccc ttcccaacag    7800
ttgcgcagcc tgaatggcga atggcgcgac gcgcctgta gcggcgcatt aagcgcggcg     7860
ggtgtggtgg ttacgcgcag cgtgaccgct acacttgcca gcgccctagc gcccgctcct    7920
ttcgctttct tcccttcctt tctcgccacg ttcgccggct ttccccgtca gctctaaat     7980 cgggggctcc ctttagggtt ccgatttagt gctttacggc acctcgaccc caaaaaactt    8040
gattagggtg atggttcacg tagtgggcca tcgccctgat agacggtttt tcgccctttg    8100
acgttggagt ccacgttctt taatagtgga ctcttgttcc aaactggaac aacactcaac    8160
cctatctcgg tctattcttt tgatttataa gggattttgc cgatttcggc ctattggtta    8220
aaaaatgagc tgatttaaca aaaatttaac gcgaatttta acaaaatatt aacgtttaca    8280
atttcctgat gcggtatttt ctccttacgc atctgtgcgg tatttcacac cgcataggca    8340
agtgcacaaa caatacttaa ataaatacta ctcagtaata acctatttct tagcattttt    8400
gacgaaattt gctattttgt tagagtcttt tacaccattt gtctccacac ctccgcttac    8460
atcaacacca ataacgccat ttaatctaag cgcatcacca acattttctg gcgtcagtcc    8520
accagctaac ataaaatgta agctttcggg gctctcttgc cttccaaccc agtcagaaat    8580
cgagttccaa tccaaaagtt cacctgtccc acctgcttct gaatcaaaca agggaataaa    8640
cgaatgaggt ttctgtgaag ctgcactgag tagtatgttg cagtcttttg gaaatacgag    8700
tcttttaata actggcaaac cgaggaactc ttggtattct tgccacgact catctccatg    8760
cagttggacg atatcaatgc cgtaatcatt gaccagagcc aaaacatcct ccttaggttg    8820
attacgaaac acgccaacca agtatttcgg agtgcctgaa ctatttttat atgcttttac    8880
aagacttgaa attttccttg caataaccgg gtcaattgtt ctctttctat tgggcacaca    8940 tataatacc cagcaagtcag catcggaatc tagagcacat tctgcggcct ctgtgctctg     9000
caagccgcaa actttcacca atggaccaga actacctgtg aaattaataa cagacatact    9060
ccaagctgcc tttgtgtgct taatcacgta tactcacgtg ctcaatagtc accaatgccc    9120
tccctcttgg ccctctcctt ttcttttttc gaccgaatta attcttaatc ggcaaaaaaa    9180
gaaaagctcc ggatcaagat tgtacgtaag gtgacaagct atttttcaat aaagaatatc    9240
ttccactact gccatctggc gtcataactg caaagtacac atatattacg atgctgtcta    9300
ttaaatgctt cctatattat atatatagta atgtcgttta tggtgcactc tcagtacaat    9360
ctgctctgat gccgcatagt taagccagcc ccgacacccg ccaacacccg ctgacgcgcc    9420
ctgacgggct tgtctgctcc cggcatccgc ttacagacaa gctgtgaccg tctccgggag    9480
ctgcatgtgt cagaggtttt caccgtcatc accgaaacgc gcga                     9524
```

MODIFIED CAS9 COMPOSITIONS AND METHODS OF USE

CROSS-REFERENCE TO RELATED APPLICATION

This application is the U.S. national phase application, pursuant to 35 U.S.C. § 371, of PCT international application Ser. No.: PCT/US2016/058719, filed Oct. 25, 2016, designating the United States and published in English, which claims the benefit of the following U.S. Provisional Application No. 62/249,113, filed Oct. 30, 2015, the entire contents of which are incorporated herein by reference.

BACKGROUND OF THE INVENTION

The Crispr/Cas9 revolution is allowing researchers to surgically disable or repair any single gene in cells and animals. The Crispr/Cas9 technology cuts a specific gene location. The repair template that is supplied must also hit the gene location at the same time. Presently, this is a random event. Consequently, such repair events have very low efficiency rates. More specifically, in contrast with the gene disabling function of Crispr/Cas9, which is greater than 80%, the gene repair function ranges from less than about 1% to under 10% depending on the system. Methods for enhancing the gene repair function of Cas9 are required.

SUMMARY OF THE INVENTION

In one aspect, the invention provides a Cas9 fusion polypeptide containing a biologically active Cas9 polypeptide fused to a tag selected from the group consisting of SNAP, CLIP, MCP, or ACP. In another aspect, the invention provides a Cas9 fusion polypeptide containing a biologically active Cas9 polypeptide fused to a SNAP tag. In one embodiment, the sequence is SEQ ID NO:2. In another aspect, the invention provides a polynucleotide encoding the polypeptide of a previous aspect. In another aspect, the invention provides an expression vector containing the polynucleotide of previous aspect. In another aspect, the invention provides a cell containing the expression vector of a previous aspect. In another aspect, the invention provides a method for enhancing transgene integration efficiency, the method involving expressing in a cell a vector encoding Cas9-SNAP, a small guide RNA, and a transgene suitable for integration into a genome. In one embodiment, the integration efficiency is increased at least about 2-fold relative to the level present in a corresponding control cell expressing wild-type Cas9.

In another aspect, the invention provides a method for enhancing Homologous DNA Recombination (HDR), the method involving expressing in a cell a vector encoding Cas9-SNAP, a small guide RNA, and a transgene suitable for integration into a genome.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Cas9 polypeptide" is meant a protein having RNA-guided DNA endonuclease enzyme associated with the CRISPR (Clustered Regularly Interspersed Palindromic Repeats) adaptive immunity system in *Streptococcus pyogenes*, among other bacteria or a fragment thereof having Cas9 biological activity.

The sequence of an exemplary Cas9 protein is provided below:

```
  1 mdkkysigld igtnsvgwav itdeykvpsk kfkvlgntdr hsikknliga llfdsgetae 61 atrlkrtarr rytrrknric ylqeifsnem akvddsffhr leesflveed kkherhpifg 121 nivdevayhe kyptiyhlrk klvdstdkad lrliylalah mikfrghfli egdlnpdnsd 181 vdklfiqlvq tynqlfeenp inasgvdaka ilsarlsksr rlenliaqlp gekknglfgn 241 lialslgltp nfksnfdlae daklqlskdt ydddldnlla qigdqyadlf laaknlsdai 301 llsdilrvnt eitkaplsas mikrydehhq dltllkalvr qqlpekykei ffdqskngya 361 gyidggasqe efykfikpil ekmdgteell vklnredllr kqrtfdngsi phqihlgelh 421 ailrrqedfy pflkdnreki ekiltfripy yvgplargns rfawmtrkse etitpwnfee 481 vvdkgasaqs fiermtnfdk nlpnekvlpk hsllyeyftv yneltkvkyv tegmrkpafl 541 sgeqkkaivd llfktnrkvt vkqlkedyfk kiecfdsvei sgvedrfnas lgtyhdllki 601 ikdkdfldne enedilediv ltltlfedre mieerlktya hlfddkvmkq lkrrrytgwg 661 rlsrklingi rdkqsgktil dflksdgfan rnfmqlihdd sltfkediqk aqvsgqgdsl 721 hehianlags paikkgilqt vkvvdelvkv mgrhkpeniv iemarenqtt qkgqknsrer 781 mkrieegike lgsqilkehp ventqlqnek lylyylqngr dmyvdgeldi nrlsdydvdh 841 ivpqsflkdd sidnkvltrs dknrgksdnv pseevvkkmk nywrqllnak litqrkfdnl
```

```
 901 tkaergglse ldkagfikrq lvetrqitkh vaqildsrmn tkydendkli revkvitlks
 961 klvsdfrkdf qfykvreinn yhhandayln avvgtalikk ypklesefvy gdykvydvrk
1021 miakseqeig katakyffys nimnffktei tlangeirkr plietngetg eivwdkgrdf
1081 atvrkvlsmp qvnivkktev qtggfskesi lpkrnsdkli arkkdwdpkk yggfdsptva
1141 ysvlvvakve kgkskklksv kellgitime rssfeknpid fleakgykev kkdliiklpk
1201 yslfelengr krmlasagel qkgnelalps kyvnflylas hyeklkgspe dneqkqlfve
1261 qhkhyldeii eqisefskry iladanldkv lsaynkhrdk pireqaenii hlftltnlga
1321 paafkyfdtt idrkrytstk evldatlihq sitglyetri dlsqlggd
```

By "Cas9 polynucleotide" is meant a nucleic acid molecule encoding a Cas9 polypeptide.

The sequence of a vector encoding human optimized Cas9 is provided below. 414-TEF1p-Cas9-CYC1t sequence 9524 bps

```
gacgaaagggcctcgtgatacgcctattttataggttaatgtcatgataataatggtttcttagacgga
tcgcttgcctgtaacttacacgcgcctcgtatctttttaatgatggaataatttgggaatttactctgtgt
ttatttattttttatgtttttgtatttggattttagaaagtaaataaagaaggtagaagagttacggaatga
agaaaaaaaataaacaaaggtttaaaaaatttcaacaaaaagcgtactttacatatatatttattagac
aagaaaagcagattaaatagatatacattcgattaacgataagtaaaatgtaaaatcacaggattttcgt
gtgtggtcttctacacagacaagatgaaacaattcggcattaatacctgagagcaggaagagcaagataa
aaggtagtatttgttggcgatcccctagagtcttttacatcttcggaaaacaaaactattttttctt
aatttctttttttactttctattttttaatttatatatttatattaaaaaatttaaattataattattttt
atagcacgtgatgaaaaggacccaggtggcacttttcggggaaatgtgcgcggaacccctatttgtttat
ttttctaaatacattcaaatatgtatccgctcatgagacaataaccctgataaatgcttcaataatattg
aaaaaggaagagtatgagtattcaacatttccgtgtcgcccttattccttttttgcggcattttgcctt
cctgttttttgctcacccagaaacgctggtgaaagtaaaagatgctgaagatcagttgggtgcacgagtgg
gttacatcgaactggatctcaacagcggtaagatccttgagagttttcgccccgaagaacgttttccaat
gatgagcacttttaaagttctgctatgtggcgcggtattatcccgtattgacgccgggcaagagcaactc
ggtcgccgcatacactattctcagaatgacttggttgagtactcaccagtcacagaaaagcatcttacgg
atggcatgacagtaagagaattatgcagtgctgccataaccatgagtgataacactgcggccaacttact
tctgacaacgatcggaggaccgaaggagctaaccgcttttttgcacaacatgggggatcatgtaactcgc
cttgatcgttgggaaccggagctgaatgaagccataccaaacgacgagcgtgacaccacgatgcctgtag
caatggcaacaacgttgcgcaaactattaactggcgaactacttactctagcttcccggcaacaattaat
agactggatggaggcggataaagttgcaggaccacttctgcgctcggcccttccggctggctggtttatt
gctgataaatctggagccggtgagcgtgggtctcgcggtatcattgcagcactggggccagatggtaagc
cctcccgtatcgtagttatctacacgacggggagtcaggcaactatggatgaacgaaatagacagatcgc
tgagataggtgcctcactgattaagcattggtaactgtcagaccaagtttactcatatatactttagatt
gatttaaaacttcattttaatttaaaaggatctaggtgaagatcctttttgataatctcatgaccaaaa
tcccttaacgtgagttttcgttccactgagcgtcagaccccgtagaaaagatcaaaggatcttcttgaga
tcctttttttctgcgcgtaatctgctgcttgcaaacaaaaaaaccaccgctaccagcggtggtttgtttg
ccggatcaagagctaccaactctttttccgaaggtaactggcttcagcagagcgcagataccaaatactg
tccttctagtgtagccgtagttaggccaccacttcaagaactctgtagcaccgcctacatacctcgctct
```

-continued

```
gctaatcctgttaccagtggctgctgccagtggcgataagtcgtgtcttaccggggttggactcaagacga tagttaccggataaggcgcagcggtcgggctgaacgggggggttcgtgcacacagcccagcttggagcgaa cgacctacaccgaactgagatacctacagcgtgagctatgagaaagcgccacgcttcccgaagggagaaa ggcggacaggtatccggtaagcggcagggtcggaacaggagagcgcacgagggagcttccagggggaaac gcctggtatctttatagtcctgtcgggtttcgccacctctgacttgagcgtcgattttttgtgatgctcgt cagggggcggagcctatggaaaaacgccagcaacgcggcctttttacggttcctggccttttgctggcc ttttgctcacatgttctttcctgcgttatcccctgattctgtggataaccgtattaccgcctttgagtga gctgataccgctcgccgcagccgaacgaccgagcgcagcgagtcagtgagcgaggaagcggaagagcgcc caatacgcaaaccgcctctccccgcgcgttggccgattcattaatgcagctggcacgacaggtttcccga ctggaaagcgggcagtgagcgcaacgcaattaatgtgagttacctcactcattaggcaccccaggcttta cactttatgcttccggctcctatgttgtgtggaattgtgagcggataacaatttcacacaggaaacagct atgaccatgattacgccaagcgcgcaattaaccctcactaaagggaacaaaagctggAGCTCATAGCTTC

AAAATGTTTCTACTCCTTTTTTACTCTTCCAGATTTTCTCGGACTCCGCGCATCGCCGTACCACTTCAAA

ACACCCAAGCACAGCATACTAAATTTCCCCTCTTTCTTCCTCTAGGGTGTCGTTAATTACCCGTACTAAA

GGTTTGGAAAAGAAAAAAGAGACCGCCTCGTTTCTTTTTCTTCGTCGAAAAAGGCAATAAAAATTTTTAT

CACGTTTCTTTTTCTTGAAAATTTTTTTTTTGATTTTTTTCTCTTTCGATGACCTCCCATTGATATTTAA

GTTAATAAACGGTCTTCAATTTCTCAAGTTTCAGTTTCATTTTTCTTGTTCTATTACAACTTTTTTTACT

TCTTGCTCATTAGAAAGAAAGCATAGCAATCTAATCTAAGTTTTCTAGAACTAGTGGATCCCCCGGGaaa aATGGACAAGAAGTACTCCATTGGGCTCGATATCGGCACAAACAGCGTCGGtTGGGCCGTCATTACGGAC

GAGTACAAGGTGCCGAGCAAAAAATTCAAAGTTCTGGGCAATACCGATCGCCACAGCATAAAGAAGAACC

TCATTGGCGCCCTCCTGTTCGACTCCGGGGAGACGGCCGAAGCCACGCGGCTCAAAAGAACAGCACGGCG

CAGATATACCCGCAGAAAGAATCGGATCTGCTACCTGCAGGAGATCTTTAGTAATGAGATGGCTAAGGTG

GATGACTCTTTCTTCCATAGGCTGGAGGAGTCCTTTTTGGTGGAGGAGGATAAAAAGCACGAGCGCCACC

CAATCTTTGGCAATATCGTGGACGAGGTGGCGTACCATGAAAAGTACCCAACCATATATCATCTGAGGAA

GAAGCTTGTAGACAGTACTGATAAGGCTGACTTGCGGTTGATCTATCTCGCGCTGGCGCATATGATCAAA

TTTCGGGGACACTTCCTCATCGAGGGGGACCTGAACCCAGACAACAGCGATGTCGACAAACTCTTTATCC

AACTGGTTCAGACTTACAATCAGCTTTTCGAAGAGAACCCGATCAACGCATCCGGAGTTGACGCCAAAGC

AATCCTGAGCGCTAGGCTGTCCAAATCCCGGCGGCTCGAAAACCTCATCGCACAGCTCCCTGGGGAGAAG

AAGAACGGCCTGTTTGGTAATCTTATCGCCCTGTCACTCGGGCTGACCCCCAACTTTAAATCTAACTTCG

ACCTGGCCGAAGATGCCAAGCTTCAACTGAGCAAAGACACCTACGATGATGATCTCGACAATCTGCTGGC

CCAGATCGGCGACCAGTACGCAGACCTTTTTTTGGCGGCAAAGAACCTGTCAGACGCCATTCTGCTGAGT

GATATTCTGCGAGTGAACACGGAGATCACCAAAGCTCCGCTGAGCGCTAGTATGATCAAGCGCTATGATG

AGCACCACCAAGACTTGACTTTGCTGAAGGCCCTTGTCAGACAGCAACTGCCTGAGAAGTACAAGGAAAT

TTTCTTCGATCAGTCTAAAAATGGCTACGCCGGATACATTGACGGCGGAGCAAGCCAGGAGGAATTTTAC

AAATTTATTAAGCCCATCTTGGAAAAAATGGACGGCACCGAGGAGCTGCTGGTAAAGCTTAACAGAGAAG

ATCTGTTGCGCAAACAGCGCACTTTCGACAATGGAAGCATCCCCCACCAGATTCACCTGGGCGAACTGCA

CGCTATCCTCAGGCGGCAAGAGGATTTCTACCCCTTTTTGAAAGATAACAGGGAAAAGATTGAGAAAATC

CTCACATTTCGGATACCCTACTATGTAGGCCCCCTCGCCCGGGGAAATTCCAGATTCGCGTGGATGACTC

GCAAATCAGAAGAGACCATCACTCCCTGGAACTTCGAGGAAGTCGTGGATAAGGGGGCCTCTGCCCAGTC

CTTCATCGAAAGGATGACTAACTTTGATAAAAATCTGCCTAACGAAAAGGTGCTTCCTAAACACTCTCTG
```

-continued

```
CTGTACGAGTACTTCACAGTTTATAACGAGCTCACCAAGGTCAAATACGTCACAGAAGGGATGAGAAAGC
CAGCATTCCTGTCTGGAGAGCAGAAGAAAGCTATCGTGGACCTCCTCTTCAAGACGAACCGGAAAGTTAC
CGTGAAACAGCTCAAAGAAGACTATTTCAAAAAGATTGAATGTTTCGACTCTGTTGAAATCAGCGGAGTG
GAGGATCGCTTCAACGCATCCCTGGGAACGTATCACGATCTCCTGAAAATCATTAAAGACAAGGACTTCC
TGGACAATGAGGAGAACGAGGACATTCTTGAGGACATTGTCCTCACCCTTACGTTGTTTGAAGATAGGGA
GATGATTGAAGAACGCTTGAAAACTTACGCTCATCTCTTCGACGACAAAGTCATGAAACAGCTCAAGAGG
CGCCGATATACAGGATGGGGGCGGCTGTCAAGAAAACTGATCAATGGGATCCGAGACAAGCAGAGTGGAA
AGACAATCCTGGATTTTCTTAAGTCCGATGGATTTGCCAACCGGAACTTCATGCAGTTGATCCATGATGA
CTCTCTCACCTTTAAGGAGGACATCCAGAAAGCACAAGTTTCTGGCCAGGGGACAGTCTTCACGAGCAC
ATCGCTAATCTTGCAGGTAGCCCAGCTATCAAAAAGGGAATACTGCAGACCGTTAAGGTCGTGGATGAAC
TCGTCAAAGTAATGGGAAGGCATAAGCCCGAGAATATCGTTATCGAGATGGCCCGAGAGAACCAAACTAC
CCAGAAGGGACAGAAGAACAGTAGGGAAAGGATGAAGAGGATTGAAGAGGGTATAAAAGAACTGGGGTCC
CAAATCCTTAAGGAACACCCAGTTGAAAACACCCAGCTTCAGAATGAGAAGCTCTACCTGTACTACCTGC
AGAACGGCAGGGACATGTACGTGGATCAGGAACTGGACATCAATCGGCTCTCCGACTACGACGTGGATCA
TATCGTGCCCCAGTCTTTTCTCAAAGATGATTCTATTGATAATAAAGTGTTGACAAGATCCGATAAAAAT
AGAGGGAAGAGTGATAACGTCCCCTCAGAAGAAGTTGTCAAGAAAATGAAAAATTATTGGCGGCAGCTGC
TGAACGCCAAACTGATCACACAACGGAAGTTCGATAATCTGACTAAGGCTGAACGAGGTGGCCTGTCTGA
GTTGGATAAAGCCGGCTTCATCAAAAGGCAGCTTGTTGAGACACGCCAGATCACCAAGCACGTGGCCCAA
ATTCTCGATTCACGCATGAACACCAAGTACGATGAAAATGACAAACTGATTCGAGAGGTGAAAGTTATTA
CTCTGAAGTCTAAGCTGGTCTCAGATTTCAGAAAGGACTTTCAGTTTTATAAGGTGAGAGAGATCAACAA
TTACCACCATGCGCATGATGCCTACCTGAATGCAGTGGTAGGCACTGCACTTATCAAAAAATATCCCAAG
CTTGAATCTGAATTTGTTTACGGAGACTATAAAGTGTACGATGTTAGGAAAATGATCGCAAAGTCTGAGC
AGGAAATAGGCAAGGCCACCGCTAAGTACTTCTTTTACAGCAATATTATGAATTTTTTCAAGACCGAGAT
TACACTGGCCAATGGAGAGATTCGGAAGCGACCACTTATCGAAACAAACGGAGAAACAGGAGAAATCGTG
TGGGACAAGGGTAGGGATTTCGCGACAGTCCGGAAGGTCCTGTCCATGCCGCAGGTAACATCGTTAAAA
AGACCGAAGTACAGACCGGAGGCTTCTCCAAGGAAAGTATCCTCCCGAAAAGGAACAGCGACAAGCTGAT
CGCACGCAAAAAAGATTGGGACCCCAAGAAATACGGCGGATTCGATTCTCCTACAGTCGCTTACAGTGTA
CTGGTTGTGGCCAAAGTGGAGAAAGGGAAGTCTAAAAAACTCAAAAGCGTCAAGGAACTGCTGGGCATCA
CAATCATGGAGCGATCAAGCTTCGAAAAAAACCCCATCGACTTTCTCGAGGCGAAAGGATATAAAGAGGT
CAAAAAAGACCTCATCATTAAGCTTCCCAAGTACTCTCTCTTTGAGCTTGAAAACGGCCGGAAACGAATG
CTCGCTAGTGCGGGCGAGCTGCAGAAAGGTAACGAGCTGGCACTGCCCTCTAAATACGTTAATTTCTTGT
ATCTGGCCAGCCACTATGAAAAGCTCAAAGGGTCTCCCGAAGATAATGAGCAGAAGCAGCTGTTCGTGGA
ACAACACAAACACTACCTTGATGAGATCATCGAGCAAATAAGCGAATTCTCCAAAAGAGTGATCCTCGCC
GACGCTAACCTCGATAAGGTGCTTTCTGCTTACAATAAGCACAGGGATAAGCCCATCAGGGAGCAGGCAG
AAAACATTATCCACTTGTTTACTCTGACCAACTTGGGCGCGCCTGCAGCCTTCAAGTACTTCGACACCAC
CATAGACAGAAAGCGGTACACCTCTACAAAGGAGGTCCTGGACGCCACACTGATTCATCAGTCAATTACG
GGGCTCTATGAAACAAGAATCGACCTCTCTCAGCTCGGTGGAGACAGCAGGGCTGACCCCAAGAAGAAGA
GGAAGGTGTGATCTCTTCTCGAGTCATGTAATTAGTTATGTCACGCTTACATTCACGCCCTCCCCCCACA
TCCGCTCTAACCGAAAAGGAAGGAGTTAGACAACCTGAAGTCTAGGTCCCTATTTATTTTTTTATAGTTA
TGTTAGTATTAAGAACGTTATTTATATTTCAAATTTTTCTTTTTTTTCTGTACAGACGCGTGTACGCATG
TAACATTATACTGAAAACCTTGCTTGAGAAGGTTTTGGGACGCTCGAAGGCTTTAATTTGCGGCCGGTAC
```

-continued

```
ccaattcgccctatagtgagtcgtattacgcgcgctcactggccgtcgttttacaacgtcgtgactggga aaaccctggcgttacccaacttaatcgccttgcagcacatccccctttcgccagctggcgtaatagcgaa gaggcccgcaccgatcgcccttcccaacagttgcgcagcctgaatggcgaatggcgcgacgcgcctgta gcggcgcattaagcgcggcgggtgtggtggttacgcgcagcgtgaccgctacacttgccagcgccctagc gcccgctcctttcgctttcttccttcctttctcgccacgttcgccggctttccccgtcaagctctaaat cgggggctccctttaggggttccgatttagtgctttacggcacctcgaccccaaaaaacttgattagggtg atggttcacgtagtgggccatcgccctgatagacggttttttcgccctttgacgttggagtccacgttctt taatagtggactcttgttccaaactggaacaacactcaaccctatctcggtctattcttttgatttataa gggattttgccgatttcggcctattggttaaaaaatgagctgatttaacaaaaatttaacgcgaatttta acaaaatattaacgtttacaatttcctgatgcggtattttctccttacgcatctgtgcggtatttcacac cgcataggcaagtgcacaaacaatacttaaataaatactactcagtaataacctatttcttagcattttt gacgaaatttgctatttttgttagagtcttttacaccatttgtctccacacctccgcttacatcaacacca ataacgccatttaatctaagcgcatcaccaacattttctggcgtcagtccaccagctaacataaaatgta agctttcggggctctcttgccttccaacccagtcagaaatcgagttccaatccaaaagttcacctgtccc acctgcttctgaatcaaacaagggaataaacgaatgaggtttctgtgaagctgcactgagtagtatgttg cagtcttttggaaatacgagtcttttaataactggcaaaccgaggaactcttggtattcttgccacgact catctccatgcagttggacgatatcaatgccgtaatcattgaccagagccaaaacatcctccttaggttg attacgaaacacgccaaccaagtatttcggagtgcctgaactatttttatatgcttttacaagacttgaa attttccttgcaataaccgggtcaattgttctctttctattgggcacacatataatacccagcaagtcag catcggaatctagagcacattctgcggcctctgtgctctgcaagccgcaaactttcaccaatggaccaga actacctgtgaaattaataacagacatactccaagctgcctttgtgtgcttaatcacgtatactcacgtg ctcaatagtcaccaatgccctccctcttggccctctccttttcttttttcgaccgaattaattcttaatc ggcaaaaaagaaaagctccggatcaagattgtacgtaaggtgacaagctattttttcaataaagaatatc ttccactactgccatctggcgtcataactgcaaagtacacatatattacgatgctgtctattaaatgctt cctatattatatatagtaatgtcgtttatggtgcactctcagtacaatctgctctgatgccgcatagt taagccagccccgacacccgccaacacccgctgacgcgccctgacgggcttgtctgctcccggcatccgc ttacagacaagctgtgaccgtctccgggagctgcatgtgtcagaggttttcaccgtcatcaccgaaacgc gcga
```

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Figure 1A:
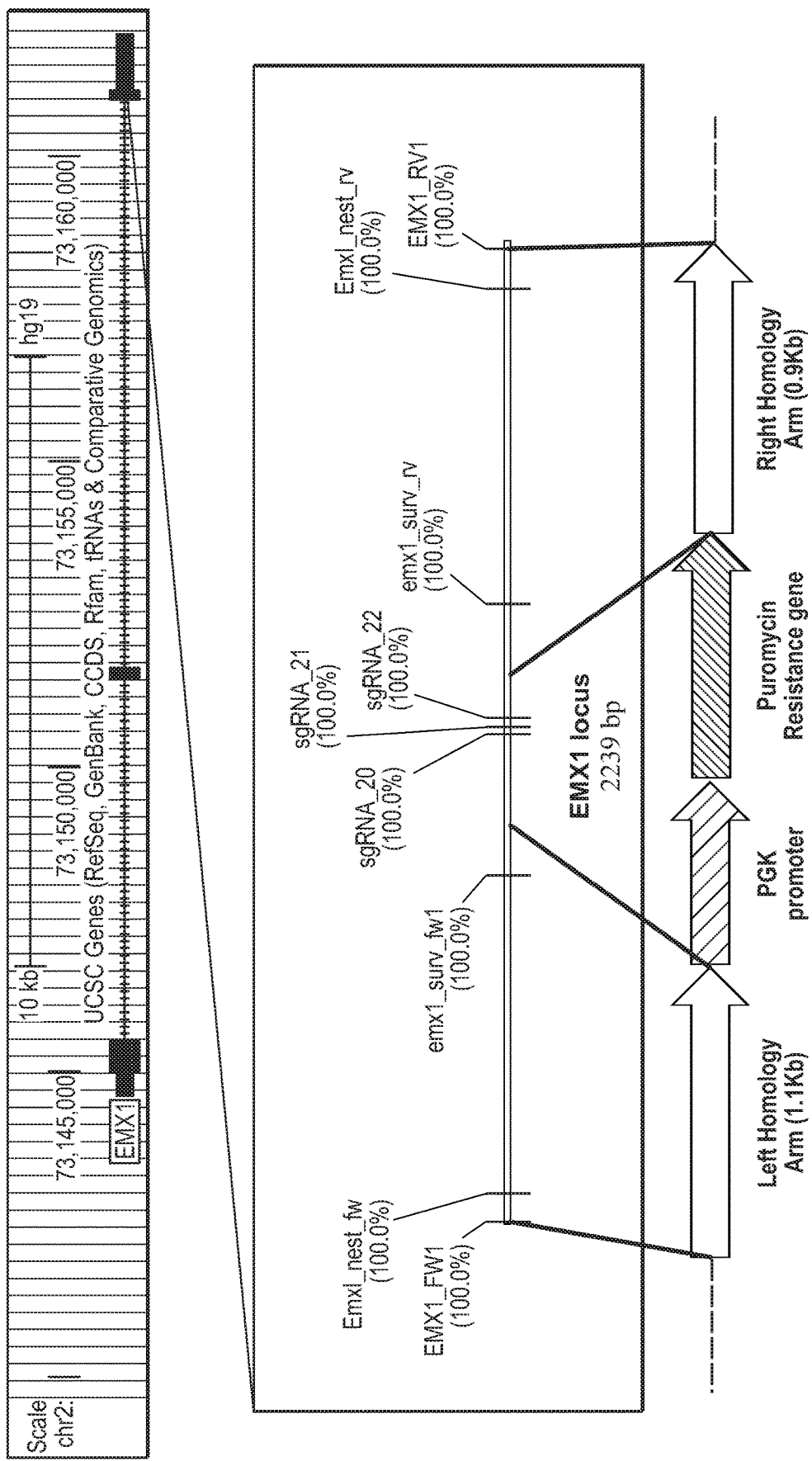
FIGS. 1A and 1B provide schematic diagrams of the EMX1 locus, and mapping that locus onto a chimeric polynucleotide that includes from 5' to 3' a left homology arm featuring 1.1 Kb of EMX1, a PGK promoter, which drives expression of the Puromycin Resistance Gene, and a right homology arm featuring 0.9 Kb of the EMX1 locus.

Sequences of the Invention hCas9-SNAP fusion nucleotide sequence
START of sequence.

(SEQ ID NO: 1)

atggacaagaagtactccattgggctcgatatcggcacaaacagcgtcggctgggccgtcattacggacgagtacaaggtgccgag caaaaaattcaaagttctgggcaataccgatcgccacagcataaagaagaacctcattggcgccctcctgttcgactccggggagacg gccgaagccacgcggctcaaaagaacagcacggcgcagatatacccgcagaaagaatcggatctgctacctgcaggagatctttag taatgagatggctaaggtggatgactctttcttccataggctggaggagtccttttttggtggaggaggataaaaagcacgagcgccacc caatctttggcaatatcgtggacgaggtggcgtaccatgaaaagtacccaaccatatatcatctgaggaagaagcttgtagacagtact gataaggctgacttgcggttgatctatctcgcgctggcgcatatgatcaaatttcggggacacttcctcatcgagggggacctgaaccc agacaacagcgatgtcgacaaactctttatccaactggttcagacttacaatcagcttttcgaagagaacccgatcaacgcatccggagt tgacgccaaagcaatcctgagcgctaggctgtccaaatcccggcggctcgaaaacctcatcgcacagctccctggggagaagaaga acggcctgtttggtaatcttatcgccctgtcactcgggctgacccccaactttaaatctaacttcgacctggccgaagatgccaagcttca actgagcaaagacacctacgatgatgatctcgacaatctgctggcccagatcggcgaccagtacgcagaccatttaggcggcaaag aacctgtcagacgccattctgctgagtgatattctgcgagtgaacacggagatcaccaaagctccgctgagcgctagtatgatcaagc gctatgatgagcaccaccaagacttgactttgctgaaggccttgtcagacagcaactgcctgagaagtacaaggaaattlicttcgatc agtctaaaaatggctacgccggatacattgacggcggagcaagccaggaggaattttacaaatttattaagcccatcttggaaaaatg gacggcaccgaggagctgctggtaaagcttaacagagaagatctgttgcgcaaacagcgcactacgacaatggaagcatccccac cagattcacctgggcgaactgcacgctatcctcaggcggcaagaggatttctaccccatagaaagataacagggaaaagattgagaa aatcctcacatttcggataccctactatgtaggcccctcgcccggggaaattccagattcgcgtggatgactcgcaaatcagaagaga ccatcactccctggaacttcgaggaagtcgtggataagggggcctctgcccagtccttcatcgaaaggatgactaactttgataaaaat ctgcctaacgaaaaggtgcttcctaaacactctctgctgtacgagtacttcacagtttataacgagctccaccaaggtcaaatacgtcaca gaagggatgagaaagccagcattcctgtctggagagcagaagaaagctatcgtggacctcctcttcaagacgaaccggaaagttacc gtgaaacagctcaaagaagactatttcaaaaagattgaatgtttcgactctgttgaaatcagcggagtggaggatcgcttcaacgcatcc ctgggaacgtatcacgatctcctgaaaatcattaaagacaaggacttcctggacaatgaggagaacgaggacattcttgaggacattgt cctcacccttacgttgtttgaagatagggagatgattgaagaacgcttgaaaacttacgctcatctcttcgacgacaaagtcatgaaaca gctcaagaggcgccgatatacaggatgggggcggctgtcaagaaaactgatcaatgggatccgagacaagcagagtggaaagaca atcctggattttcttaagtccgatggatttgccaaccggaacttcatgcagttgatccatgatgactctctcaccttttaaggaggacatcca gaaagcacaagtttctggccaggggacagtcttcacgagcacatcgctaatcttgcaggtagcccagctatcaaaaagggaatactg cagaccgttaaggtcgtggatgaactcgtcaaagtaatgggaaggcataagcccgagaatatcgttatcgagatggcccgagagaac caaactacccagaagggacagaagaacagtagggaaaggatgaagaggattgaagagggtataaaagaactggggtcccaaatcc ttaaggaacacccagttgaaaacacccagcttcgaatgagaagctctacctgtactacctgcagaacggcagggacatgtacgtgga tcaggaactggacatcaatcggctctccgactacgacgtggatcatatcgtgccccagtcttttctcaaagatgattctattgataataaag tgttgacaagatccgataaaaatagagggaagagtgataacgtcccctcagaagaagttgtcaagaaaatgaaaaattattggcggca gctgctgaacgccaaactgatcacacaacggaagttcgataatctgactaaggctgaacgaggtggcctgtctgagttggataaagcc ggcttcatcaaaaggcagcttgttgagacacgccagatcaccaagcacgtggcccaaattctcgattcacgcatgaacaccaagtacg atgaaaatgacaaactgattcgagaggtgaaagttattactctgaagtctaagctggtctcagatttcagaaaggactttcagttnataag gtgagagagatcaacaattaccaccatgcgcatgatgcctacctgaatgcagtggtaggcactgcacttatcaaaaaatatcccaagct tgaatctgaatttgtnacggagactataaagtgtacgatgttaggaaaatgatcgcaaagtctgagcaggaaataggcaaggccaccg ctaagtacttcttnacagcaatattatgaattattcaagaccgagattacactggccaatggagagattcggaagcgaccacttatcgaa acaaacggagaaacaggagaaatcgtgtgggacaagggtagggatttcgcgacagtccggaaggtcctgtccatgccgcaggtga acatcgttaaaaagaccgaagtacagaccggaggcttctccaaggaaagtatcctcccgaaaaggaacagcgacaagctgatcgca -continued cgcaaaaaagattgggaccccaagaaatacggcggattcgattctcctacagtcgcttacagtgtactggttgtggccaaagtggaga aagggaagtctaaaaaactcaaaagcgtcaaggaactgctgggcatcacaatcatggagcgatcaagcttcgaaaaaaaccccatcg actnctcgaggcgaaaggatataaagaggtcaaaaaagacctcatcattaagcttcccaagtactctctcntgagcttgaaaacggcc ggaaacgaatgctcgctagtgcgggcgagctgcagaaaggtaacgagctggcactgccctctaaatacgttaatttcttgtatctggcc agccactatgaaaagctcaaagggtctcccgaagataatgagcagaagcagctgttcgtggaacaacacaaacactaccttgatgag atcatcgagcaaataagcgaattctccaaaagagtgatcctcgccgacgctaacctcgataaggtgctnctgcttacaataagcacag ggataagcccatcagggagcaggcagaaaacattatccacttgtnactctgaccaacttgggcgcgcctgcagccttcaagtacttcg acaccaccatagacagaaagcggtacacctctacaaaggaggtcctggacgccacactgattcatcagtcaattacggggctctatga aacaagaatcgacctctctcagctcggtggagacagcagggctgaccccaagaagaagaggaaggtggctagcatggacaaagac tgcgaaatgaagcgcaccaccctggatagccctctgggcaagctggaactgtctgggtgcgaacagggcctgcaccgtatcatcttc ctgggcaaaggaacatctgccgccgacgccgtggaagtgcctgccccagccgccgtgctgggcggaccagagccactgatgcag gccaccgcctggctcaacgcctactttcaccagcctgaggccatcgaggagttccctgtgccagccctgcaccacccagtgttccagc aggagagctttacccgccaggtgctgtggaaactgctgaaagtggtgaagttcggagaggtcatcagctacagccacctggccgccc tggccggcaatcccgccgccaccgccgccgtgaaaaccgccctgagcggaaatcccgtgcccattctgatcccctgccaccgggtg gtgcagggcgacctggacgtggggggctacgagggcgggctcgccgtgaaagagtggctgctggcccacgagggccacagact gggcaagcctgggctgggtgcggccgcactcgagcaccaccaccaccaccac
END of sequence.

hCas9-SNAP fusion polypeptide sequence
START of sequence.
(SEQ ID NO: 2)

mdkkysigldigtnsvgwavitdeykvpskkfkvlgntdrhsikknligallfdsgetaeatartarrrytaknricylqeifsne makvddsffhrleesflveedkkherhpifgnivdevayhekyptiyhlrkklvdstdkadlrliylalahmikfrghfliegdlnp dnsdvdklfiqlvqtynqlfeenpinasgvdakailsarlsksalenliaqlpgekknglfgnlialslgltpnfksnfdlaedaklqls kdtydddldnllaqigdqyadlflaaknlsdaillsdilrvnteitkaplsasmikrydehhqdltllkalvrqqlpekykeiffdqskn gyagyidggasqeefykfikpilekmdgteellvklnredllrkqrtfdngsiphqihlgelhailaqedfypflkdnrekiekiltfri pyyvgplargnsrfawmtrkseetitpwnfeevvdkgasaqsfiermtnfdknlpnekvlpkhsllyeyftvyneltkvkyvteg mrkpaflsgeqkkaivdllfktnrkvtvkqlkedyfkkiecfdsveisgvedrfnaslgtyhdllkiikdkdfldneenedilediv lt ltlfedremieerlktyahlfddkvmkqlkarytgwgrlsrklingirdkqsgktildflksdgfanramqlihddsltfkediqka qvsgqgdslhehianlagspaikkgilqtvkvvdelvkvmgrhkpeniviemarenqttqkgqknsrermkrieegikelgsqil kehpventqlqneklylyylqngrdmyvdqeldinrlsdydvdhivpqsflkddsidnkvltrsdknrgksdnvpseevvkkm knywrqllnaklitqrkfdnitkaergglseldkagfikrqlvetrqitkhvaqildsrmntkydendklirevkvitlksklvsdfrkd fqfykvreinnyhhandaylnavvgtalikkypkles efvygdykvydvrkmiakseqeigkatakyffysnimnffkteitlan geirkrplietngetgeivwdkgrdfatvrkvlsmpqvnivkktevqtggfskesilpkrnsdkliarkkdwdpkkyggfdsptva ysvlvvakvekgkskklksvkellgitimerssfeknpidfleakgykevkkdliiklpkyslfelengrkrmlas agelqkgnela lpskyvnflylashyeklkgspedneqkqlfveqhkhyldeiieqisefskrviladanldkvlsaynkhrdkpireqaeniihlftlt nlgapaafkyfdttidrkrytstkevldatlihqsitglyetridlsqlggdsradpkkkrkvas mdkdcemkrttldsplgklelsgce qglhriiflgkgts aadavevpapaavlggpeplmqatawlnayfhqpeaieefpvpalhhpvfqqesftrqvlwkllkvvkfge visyshlaalagnpaataavktalsgnpvpilipchrvvqgdldvggyegglavkewllaheghrlgkpglgaaalehhhhhh
END of sequence.

DETAILED DESCRIPTION OF THE INVENTION

The invention features CAS9 fusion polypeptides and methods of use.

Like other revolutionary biotechnologies such as RNA interference, CRISPR is a natural genome control pathway but with a unique industrial origin story. CRISPR was first discovered in 2007 by scientists at Danisco, the producers of the Dannon yogurt brand, in natural strains of bacteria cultures that were cultivated for yogurt production (Barrangou et al, 2007). It is a natural immune response used by bacteria to cut the DNA of invading bacterial viruses like bacteriophage, and therefore plays an important role for industrial bacteria survival.

Recently, scientists have taken the most essential components of the bacterial CRISPR system, the Cas9 protein and the small guide RNA (sgRNA), and tailored them for genome modification. The simplicity and versatility of the CRISPR-based technology to cut any gene in animal and plant genomes with precision has been heralded as a breakthrough towards creating designer cells and model organisms at an unprecedented speed and cost-effectiveness. Additionally, animals besides mice that were previously refractory to embryonic stem cell modifications, such as rats and primates, are now able to be modified using this technology.

Due to these advantages, the journal SCIENCE (Pennissi, 2013) and the New York Times (Pollack, 2014) reported the rapid emergence of CRISPR-based genome modification technologies as a revolution in gene therapy and biomedicine. For example, genetically modifying mice for biomedical research currently requires several years for selection and modification of embryonic stem cells and selective breeding. With CRISPR-based genomic modification, mutations and transgene integrations can be generated immediately in the founder lines upon embryo manipulation, shaving years of time that would have been needed using the stem cell methods.

Multiple biotech reagents companies like Origene, Life Technologies, and Sigma have licensed CRISPR-based products for sale; while in 2013, the plasmids in highest demand from Addgene were the CRISPR-based vectors. The founders of the modified CRISPR system have also formed several biotech companies establishing CRISPR as a platform technology to generate genetically modified animals and plants. These startups include Editas, Caribou Biosciences and Horizon Discovery that are tailoring CRISPR-based technologies to generate cell lines and animal models for disease and pharmaceutical-based studies.

The CRISPR technology is competing with older legacy genome modifying enzymes like TALENS, Zinc Finger Nucleases, and Meganucleases, which are still being sold by Sangamo and Cellectis. However, the main advantage of the CRISPR system is that only one protein, Cas9, conducts the DNA cleavage, while it is the small guide RNA that specifies the targeting. The sgRNA is effortless to design for any other target sequence, contrasting with much more laborious designs and construction procedures for each protein representing the TALEN, ZFN, or Meganucleases.

The present invention provides important improvements to the CRISPR technology and tailors the system to improve Homologous DNA Recombination (HDR) with a transgene directly tethered to the Cas9 enzyme. Although the standard CRISPR technology can improve by several fold HDR from its initially very inefficient step (>0.01% to now ~5%), it is still too low to be considered robust enough for a platform technology. We believe the tethered transgene to the Cas9-SNAP element will increase this to at least about 10%, 15%, 20% or more which provides the efficiency desired to allow it to be a platform technology for broad market use.

Tags

The invention provides Cas9 fusion proteins. In particular, Cas9 is fused to one or more of the following tags (e.g., SNAP, CLIP, ACP, MCP).

SNAP-tag is a 20 kDa mutant of the DNA repair protein $O^6$-alkylguanine-DNA alkyltransferase that reacts specifically and rapidly with benzylguanine (BG) derivatives, leading to irreversible covalent labeling of the SNAP-tag with a synthetic probe. SNAP-tag has a number of features that make it ideal for a variety of applications in protein labeling. The rate of the reaction of SNAP-tag with BG derivatives is to a large extent independent of the nature of the synthetic probe attached to BG, permitting the labeling of SNAP fusion proteins with a wide variety of synthetic probes. Second, SNAP-tag has no restrictions with respect to cellular localization and expression host. Third, SNAP-tag substrates are chemically inert towards other proteins, avoiding nonspecific labeling in cellular applications. Finally, many SNAP-tag substrates are cell permeable, permitting labeling of intracellular proteins in live cells.

The CLIP-tag can also be used to tag CAS9. The CLIP-tag was created by engineering the substrate specificity of the SNAP-tag, permitting it to react specifically with $O_2$-benzylcytosine (BC) derivatives. Since the SNAP- and CLIP-tags specifically react with orthogonal substrates, SNAP and CLIP fusion proteins can be labeled simultaneously and specifically with different synthetic probes in living cells. One application of the CLIP-tag is dual-labeling of fusion proteins in conjunction with the SNAP-tag.

A third method tagging method is based on an enzyme-catalyzed post-translational modification. The protein of interest is fused to an acyl carrier protein (ACP) and the corresponding fusion protein is specifically labeled with CoA derivatives through a post-translational modification catalyzed by the phosphopantetheinyl transferase AcpS. An interesting feature of the ACP-tag is its small size of 9 kDa. In addition, a mutant of ACP, called MCP, is labeled by the phosphopantetheinyl transferase Sfp but not by AcpS, thereby permitting the selective labeling of ACP and MCP fusion proteins with different probes in one sample. In contrast to several of the substrates of the SNAP- and CLIP-tag, substrates of the ACP-tag are not cell permeable; therefore this approach is best suited for the labeling of cell surface proteins.

Any of SNAP-tag, CLIP-tag, MCP-tag and ACP-tag can be fused to CAS9.

The invention features compositions comprising a Cas9-SNAP and methods that are useful for enhancing homologous DNA Recombination (HDR) using a transgene directly tethered to the Cas9 enzyme.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

EMX1 Chimeric Transgene

Figure 1B:
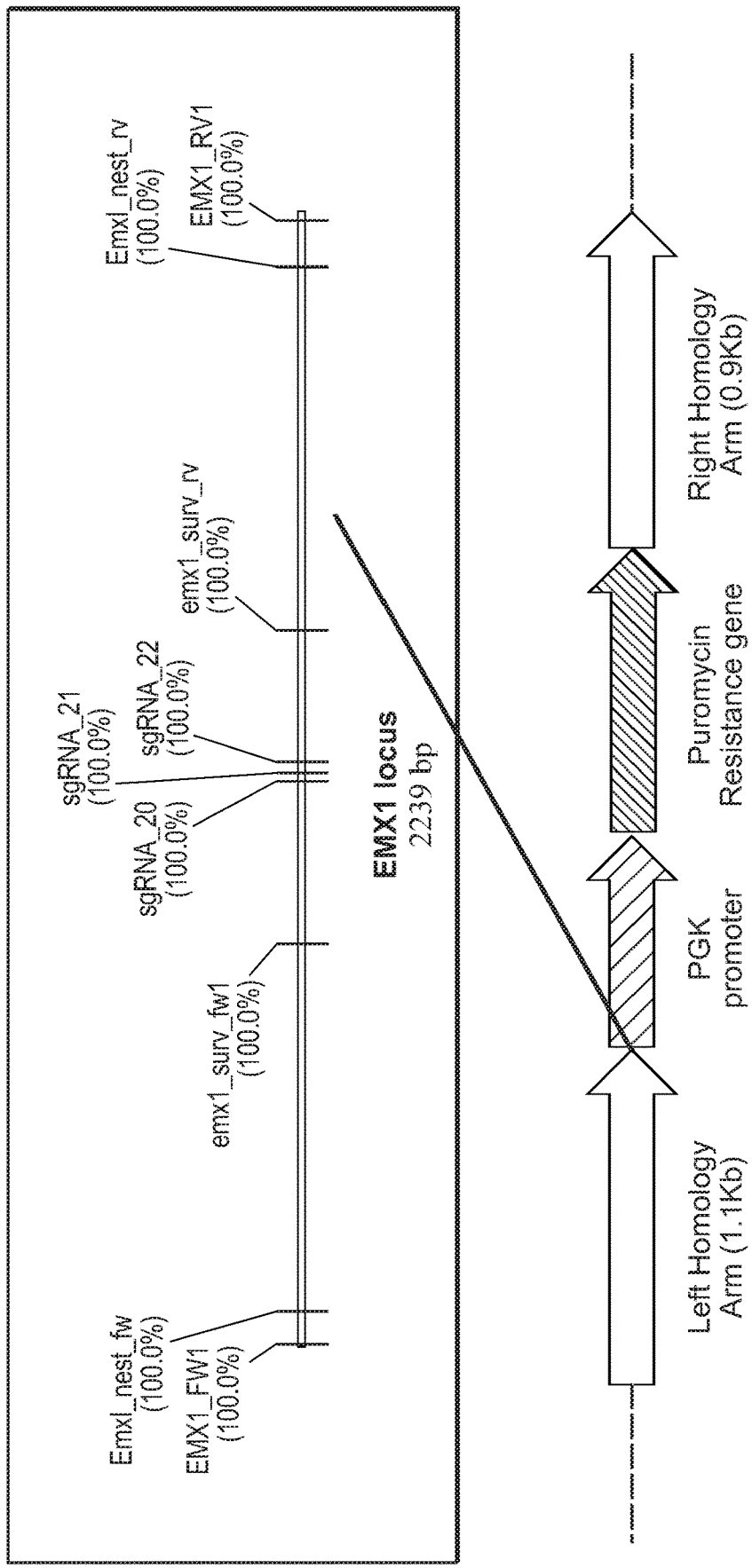

There is a need for better gene-repair and tagging technologies for therapy and disease research. The market for an improved product to conduct gene-repair and tagging could be large, since no other technology exists for this. The current technology consists of artificial transgenes, extra copies that do not fully match the natural gene. The Crispr/Cas9 technology can cut a specific gene location, but the repair template that is supplied must also hit the gene location at the same time: a random event that explains the currently very low efficiency rates in the repair event. Without wishing to be bound by theory, it is likely that a re-engineered form of Cas9 physically brings the repair template with it to the target gene location, therefore greatly increasing repair efficiency. No other description of this design has been reported. A puromycin resistance gene is integrated into an EmxI locus to assess transgene integration efficiency (FIGS. 1A and 1B).

Example 2

Determine the Efficiency of Gene Repair with the Cas9SNAP Technology

The current CRISPR/Cas9 system has generated a lot of excitement in biomedical research because it can efficiently generate deletions and substitution mutations as the main outcome from Non-Homologous End Joining (NHEJ) DNA repair of a locus cut by Cas9/sgRNA. However, insertion of a homologous segment of a new DNA transgene after Cas9 targeting remains inefficient, even though this is a highly desired outcome to complement the needs of generating loss-of-function mutations.

Figure 2:
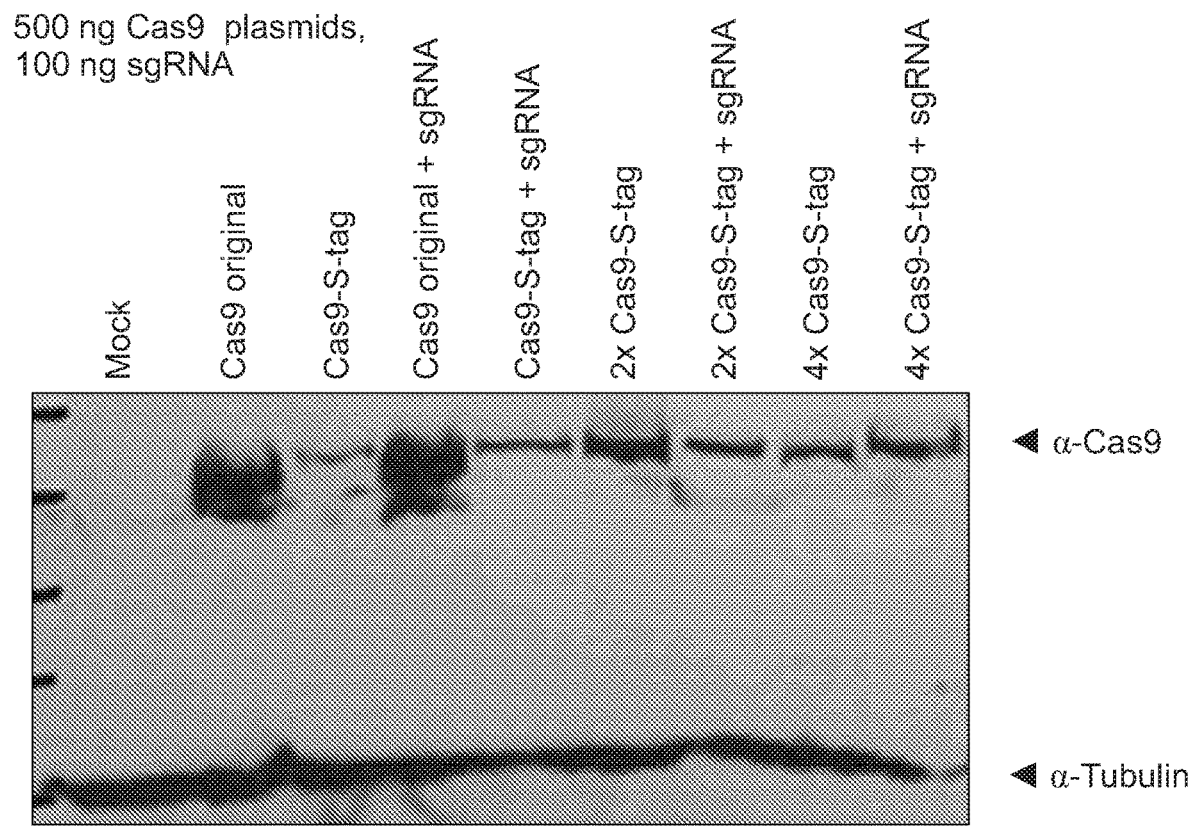
FIG. 2 is a Western blot. Human embryonic kidney (HEK) cells were transfected with 500 ng of a plasmid encoding wild-type Cas9 (original) or Cas9 fused to a SNAP (S)-tag and a plasmid encoding a small guide RNA (sgRNA). The cells were homogenized and the protein extracts were separated using standard Western blot techniques. The blot was then probed with an antibody for anti-Cas9 and an anti-tubulin antibody, which was used as a control for protein loading. As indicated the Cas9 protein is abundantly expressed in HEK cells, whether or not the sgRNA was also expressed. In contrast, Cas9-S-tag was present at much lower levels. Without wishing to be bound by theory, it is likely that Cas9-S-tag has greater turnover than wild-type Cas9.
Figure 3A:
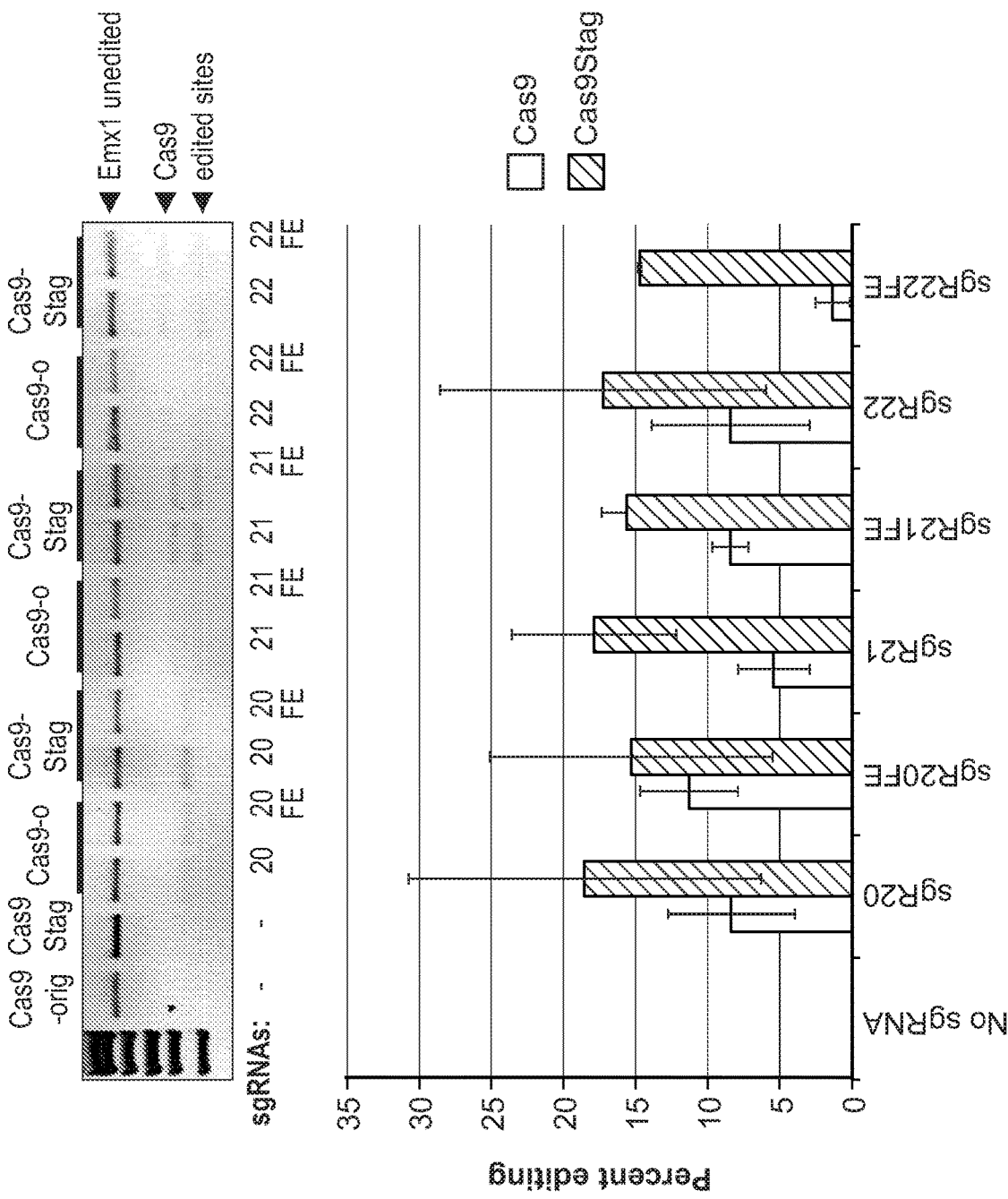
FIG. 3 includes an agarose gel and a bar graph. Surprisingly, even though the Cas9-S was present in protein extracts at lower levels than wild-type, it showed much better genome editing activity.

The first step in increasing transgene integration was to clone the SNAP-tag to the Cas9 protein which creates a method to connect the transgene to the Cas9 protein. We have successfully cloned and expressed the modified Cas9-SNAP protein in HEK293T cells (FIG. 2). Several sgRNAs targeting the EmxI locus of the HEK293T cells have also been cloned and expressed (FIG. 2). To test activity of the reconstituted system, the protein and sgRNAs were transfected into HEK293T cells and genomic DNA cleavage assessed (FIG. 3A). Indel production was analyzed using the Surveyor Assay with both the native Cas9 protein and our modified Cas9-SNAP protein. Unexpectedly, when Cas9-SNAP is expressed as the nuclease, there is approximately a two-fold increase in indel frequency versus the unmodified Cas9. We did not design the Cas9-SNAP protein with the intent of increasing indel frequency, but chose the SNAP tag because of its ability to covalently bond with benzylguanine (BG) which will allow the connection of the transgene to the protein. However the SNAP tag can function as a weak DNA binder, since it is a mutated form of a DNA repair protein. Without wishing to be bound by theory, this may explain the increase we see in indel frequency as it is likely that the SNAP tag stabilizes the Cas9 on the genomic target, allowing it more time to cleave the locus than it would have without the stabilization, therefore increasing the efficiency.

FIG. 3A shows that Cas9-SNAP shows better genome editing activity than wild-type Cas9.

Example 3

A Two-Fold Increase in Transgene Integration Efficiency is Observed when Cas9-SNAP is Used A puromycin resistance assay was conducted. As described above, a puromycin resistance gene was integrated into the EmxI locus, and transgene integration efficiency was measured by the survival of cell colonies after a two week treatment with puromycin. This assay allowed us to measure transgene integration efficiency.

Figure 3B:
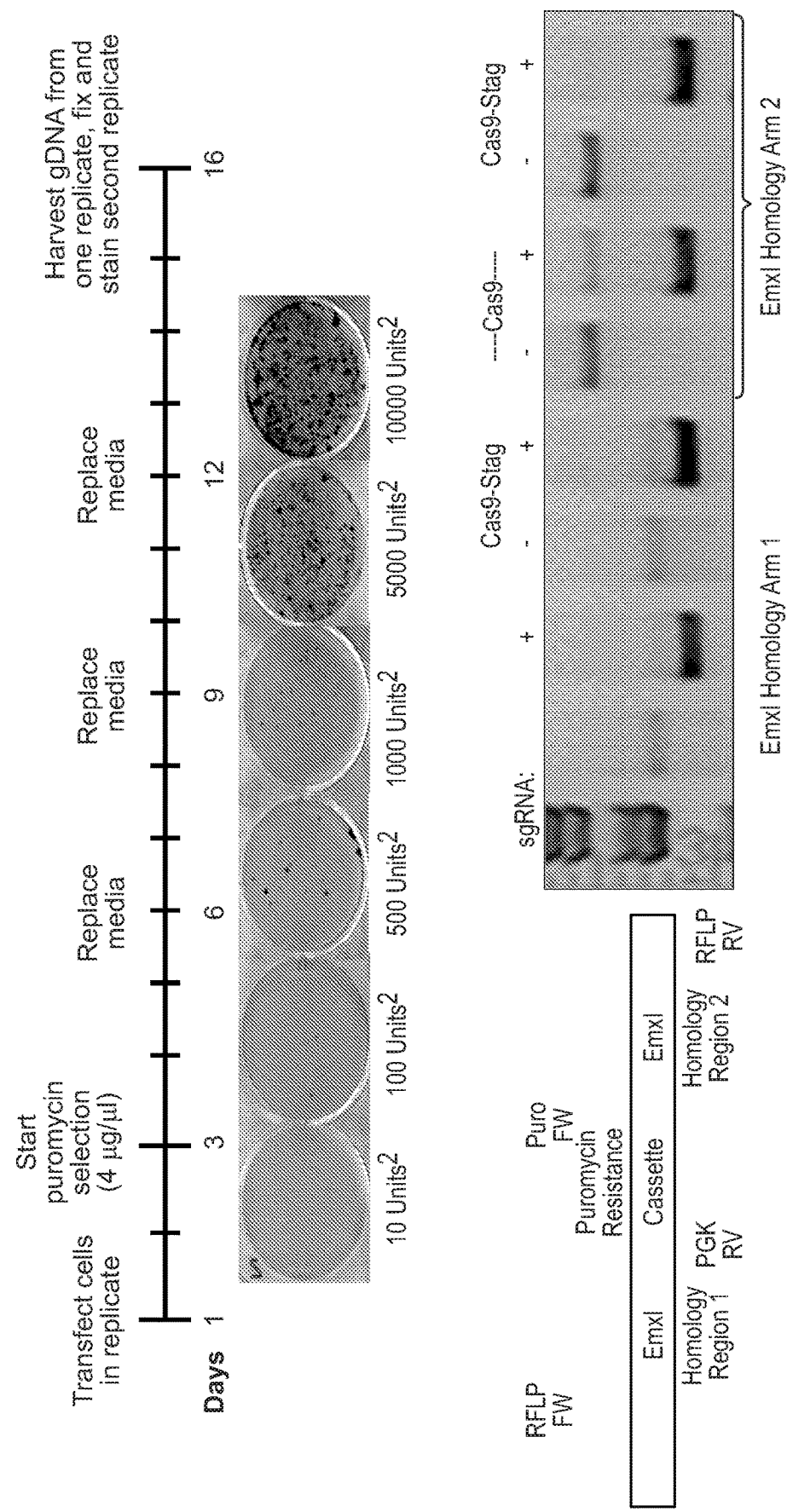

We have performed the puromycin assay with a variety of different transgene substrates in order to determine which will allow for the highest transgene integration efficiency. Two weeks after puromycin selection, the surviving cell colonies are stained and can be visualized as seen in FIG. 3B. The area of cells remaining can be compared to evaluate the optimum conditions for transgene insertion, with a higher area of surviving cells correlating to higher transgene integration efficiency. We have also determined by PCR analysis that the survival is due to insertion of the puromycin resistance gene inside the targeted EmxI locus as opposed to transient expression or off-target insertion as shown in FIG. 3B. Cells lacking the sgRNA can survive, but the puromycin resistance gene isn't correctly targeted to the EmxI locus.

Figure 4:
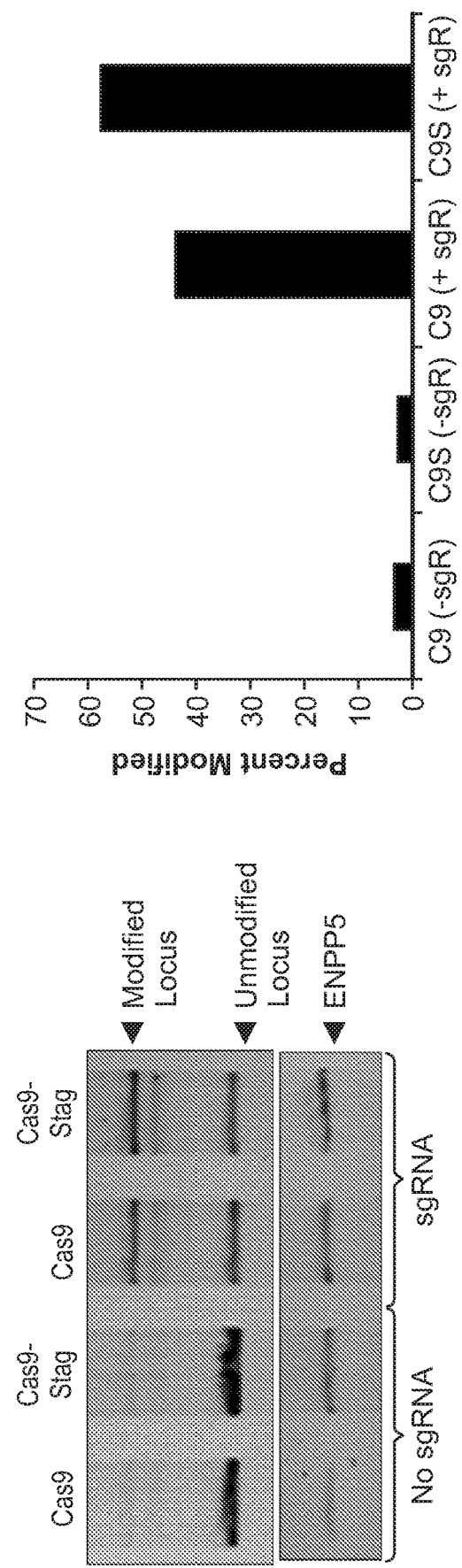
FIG. 4 is an agarose gel and a bar graph. The agarose gel shows that the modified EMX locus is observed at high levels in HEK cells that express sgRNA and Cas9 (C9) or Cas9-S.

FIG. 4 shows that puromycin selection and Cas9 or Cas9-SNAP creates HDR-modified cells.

Figure 5:
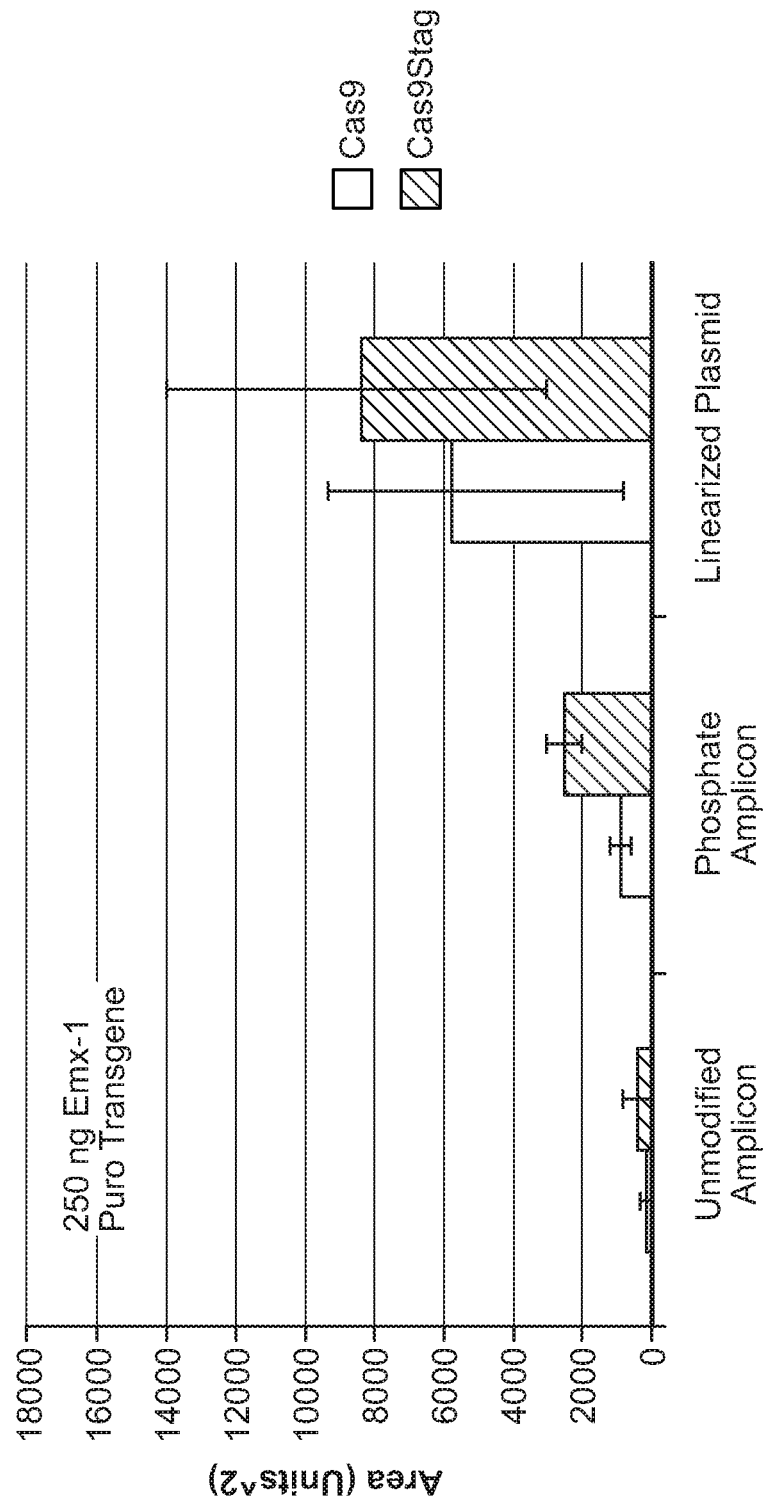
FIG. 5 is a bar graph showing that homology detected repair (HDR) is not increased with untethered transgenes.

FIG. 5 shows results of testing PCR amplicon transgene with 5' phosphates and linearized plasmid to see whether they allow a higher level of transgene integration.

Figure 6:
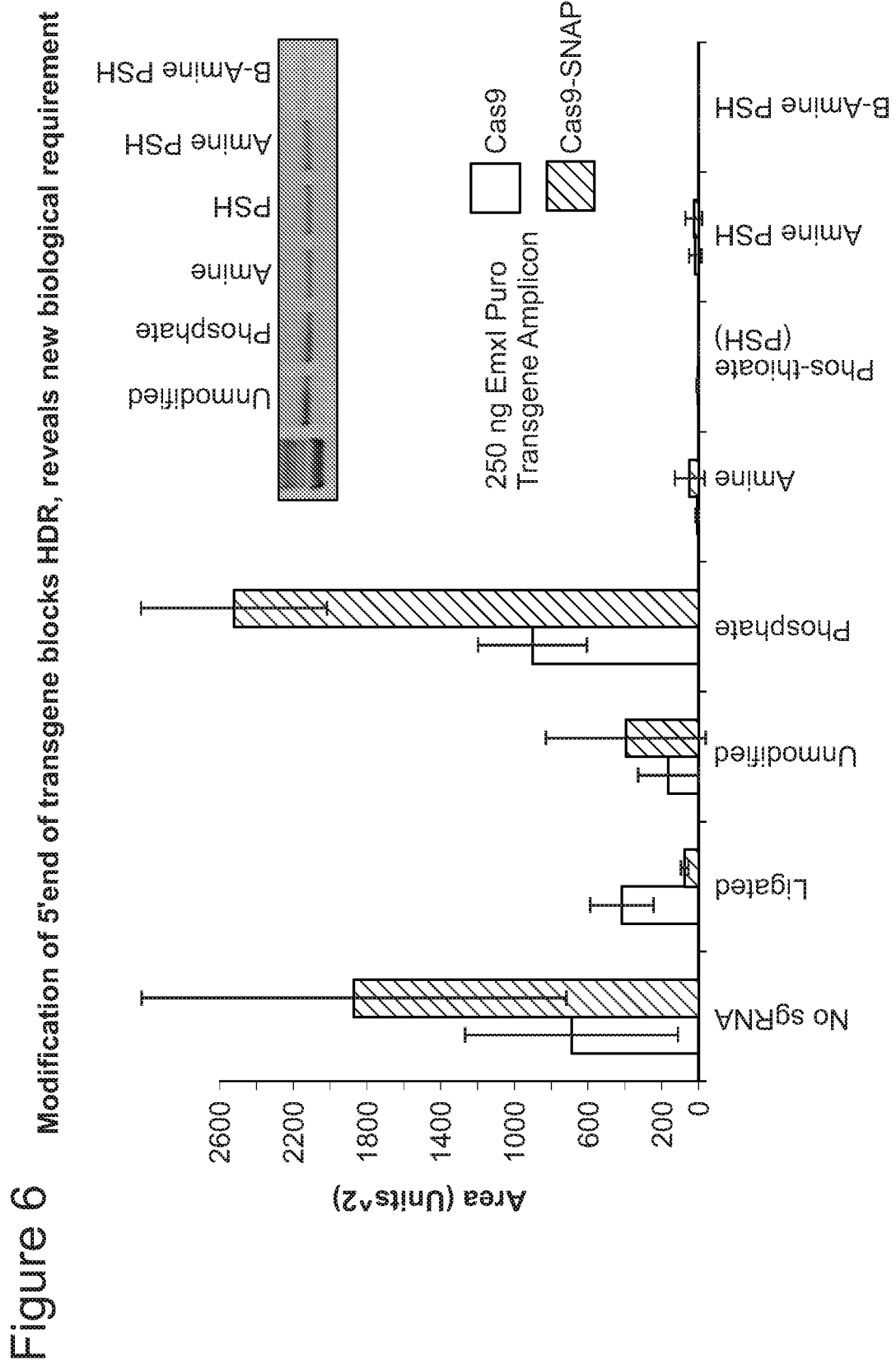
FIG. 6 is a bar graph showing that modification of the 5' end of the transgene blocks homology detected repair (HDR). In the absence of sgRNA integration events occur at random. Levels of integration are shown for ligated, unmodified, and phosphorylated 5' ends of PCR amplified transgenes. Levels of integration are virtually undetectable when the 5' end of the amplicon, is modified with amine, phosphothioate (PSH), amine phosphothioate, or B-amine PSH.

Having established the puromycin resistance assay as a reliable measure of transgene integration efficiency, we tested whether the efficiency would improve with BG coupled transgenes that would be able to bind to Cas9-SNAP and therefore be directly targeted to the cut site. However upon puromycin selection of the cells transfected with the BG modified transgene, there was no survival of any cell colonies. Further investigation showed that when any PCR amplicon transgene with either an Amine modified 5' end or internal 5' phosophorothioates was used as the transgene, no to very little cell survival after puromycin selection as seen in FIG. 6 indicating very low transgene integration efficiency.

To date, plasmid DNA is the most efficient transgene and results in the most cell survival after selection, indicating that it has the highest integration efficiency in the system. In accordance with a two-fold increase in indel frequency, there is also approximately a two-fold increase in transgene integration efficiency when Cas9-SNAP is used as the nuclease. This most likely is explained by the increase in genomic DNA cutting ability giving more opportunity for the site to be repaired by the introduced transgene.

Figure 7:
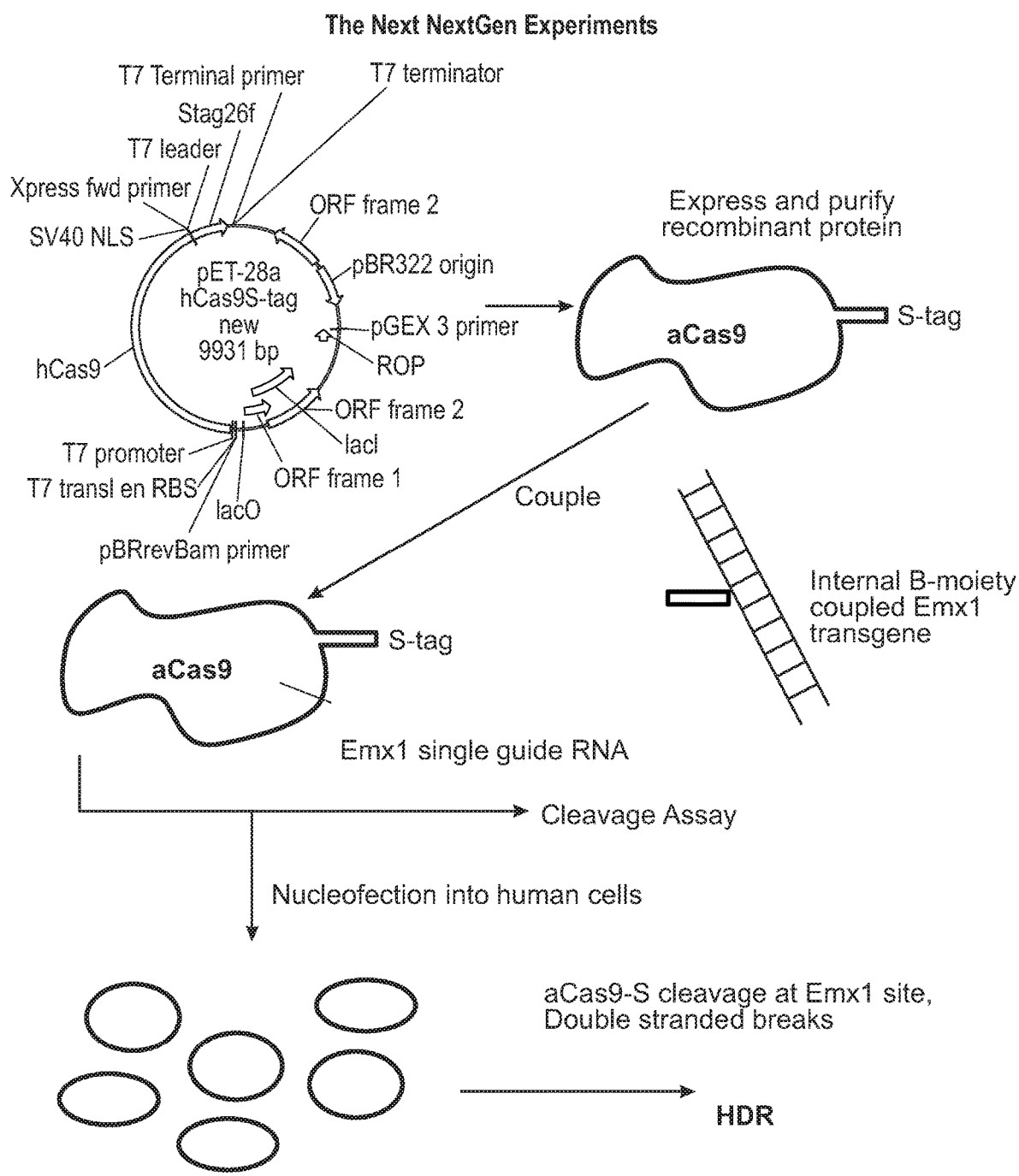
FIG. 7 is a schematic showing a workflow for future experiments.

FIG. 7 shows directions for future experiments.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A Cas9 fusion polypeptide having the sequence of SEQ ID NO:2.

2. A polynucleotide encoding the polypeptide of claim 1.

3. An expression vector comprising the polynucleotide of claim 2.

4. A cell comprising the expression vector of claim 3.

5. A method for enhancing transgene integration efficiency, the method comprising expressing in a cell a vector encoding the polypeptide of claim 1, a small guide RNA, and a transgene suitable for integration into a genome.

6. The method of claim 5, wherein the integration efficiency is increased at least about 2-fold relative to the level present in a corresponding control cell expressing wild-type Cas9.

7. A method for enhancing Homologous DNA Recombination (HDR), the method comprising expressing in a cell vector encoding the polypeptide of claim 1, a small guide RNA, and a transgene suitable for integration into a genome.

* * * * *